US009278094B2

(12) United States Patent
Bear et al.

(10) Patent No.: US 9,278,094 B2
(45) Date of Patent: *Mar. 8, 2016

(54) TREATMENTS FOR DEPRESSION AND OTHER DISEASES WITH A LOW DOSE AGENT

(71) Applicant: PharmoRx Therapeutics, Inc., Westborough, MA (US)

(72) Inventors: David M. Bear, Weston, MA (US); Robert M. Kessler, Nashville, TN (US)

(73) Assignee: PHARMORX THERAPEUTICS, INC., Westborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/639,797

(22) Filed: Mar. 5, 2015

(65) Prior Publication Data
US 2015/0202199 A1 Jul. 23, 2015

Related U.S. Application Data

(63) Continuation-in-part of application No. 14/410,551, filed as application No. PCT/US2014/013874 on Jan. 30, 2014.

(60) Provisional application No. 61/758,551, filed on Jan. 30, 2013, provisional application No. 61/814,476, filed on Apr. 22, 2013.

(51) Int. Cl.
A61K 31/497 (2006.01)
A61K 31/485 (2006.01)
A61K 31/496 (2006.01)
A61K 45/06 (2006.01)
A61K 31/135 (2006.01)
A61K 31/137 (2006.01)
A61K 31/138 (2006.01)
A61K 31/15 (2006.01)
A61K 31/165 (2006.01)
A61K 31/343 (2006.01)
A61K 31/381 (2006.01)
A61K 31/4045 (2006.01)
A61K 31/428 (2006.01)
A61K 31/4406 (2006.01)
A61K 31/4525 (2006.01)
A61K 31/454 (2006.01)

(52) U.S. Cl.
CPC .............. *A61K 31/485* (2013.01); *A61K 31/135* (2013.01); *A61K 31/137* (2013.01); *A61K 31/138* (2013.01); *A61K 31/15* (2013.01); *A61K 31/165* (2013.01); *A61K 31/343* (2013.01); *A61K 31/381* (2013.01); *A61K 31/4045* (2013.01); *A61K 31/428* (2013.01); *A61K 31/4406* (2013.01); *A61K 31/454* (2013.01); *A61K 31/4525* (2013.01); *A61K 31/496* (2013.01); *A61K 45/06* (2013.01)

(58) Field of Classification Search
None
See application file for complete search history.

(56) References Cited

U.S. PATENT DOCUMENTS

| 5,028,612 | A | 7/1991 | Glover |
|---|---|---|---|
| 5,512,593 | A | 4/1996 | Dante et al. |
| 5,817,656 | A | 10/1998 | Beasley et al. |
| 5,817,665 | A | 10/1998 | Dante |
| 5,958,962 | A | 9/1999 | Cook |
| 6,001,848 | A | 12/1999 | Noble |
| 6,001,861 | A | 12/1999 | Oertel et al. |
| RE36,547 | E | 2/2000 | Crain et al. |
| 6,034,091 | A | 3/2000 | Dante |
| 6,716,854 | B2 | 4/2004 | McBrinn et al. |
| 6,765,010 | B2 | 7/2004 | Crain et al. |
| 7,384,653 | B2 | 6/2008 | Wright et al. |
| 2002/0156056 | A1 | 10/2002 | Johnson |
| 2003/0087896 | A1 | 5/2003 | Glover |
| 2004/0242974 | A1 | 12/2004 | Glover |
| 2005/0037983 | A1 | 2/2005 | Dinan et al. |
| 2006/0069086 | A1 | 3/2006 | Michalow |
| 2007/0041905 | A1 | 2/2007 | Hoffman et al. |
| 2007/0099947 | A1 | 5/2007 | Dean, III et al. |
| 2007/0179168 | A1 | 8/2007 | Cowley et al. |
| 2007/0259939 | A1 | 11/2007 | Stebbing |
| 2008/0045610 | A1 | 2/2008 | Michalow |
| 2008/0214592 | A1 | 9/2008 | Cowley et al. |

(Continued)

FOREIGN PATENT DOCUMENTS

| EP | 451009 | 10/1991 |
|---|---|---|
| EP | 687175 | 10/2001 |

(Continued)

OTHER PUBLICATIONS

Busner et al. "The Clinical Global Impressions Scale: Applying a Research Tool in Clinical Practice". Psychiatry 2007, pp. 29-37).*
Cusin et al. "Chapter 2: Rating Scales for Depression". Handbook of Clinical Rating Scales and Assessment in Psychiatry and Mental Health. 2010. pages 7-24.*

(Continued)

*Primary Examiner* — Layla Soroush
(74) *Attorney, Agent, or Firm* — Morgan, Lewis & Bockius LLP

(57) ABSTRACT

The present invention relates to improved compositions and methods for the treatment or prevention of various diseases, including forms of depression, including, for example, breakthrough depression and treatment-refractory depression, and other mood disorders, as well as Parkinson's disease, bipolar disorder, bipolar disorder, attention deficit disorder (ADHD), Restless Leg Syndrome (RLS), and obesity. In some embodiments, the compositions and methods comprise low dose naltrexone or related opioid antagonists.

14 Claims, 6 Drawing Sheets

(56) References Cited

U.S. PATENT DOCUMENTS

| | | |
|---|---|---|
| 2010/0168119 A1 | 7/2010 | Bear et al. |
| 2012/0107396 A1 | 5/2012 | Khan |

FOREIGN PATENT DOCUMENTS

| | | |
|---|---|---|
| EP | 1870096 | 12/2007 |
| EP | 2007388 | 12/2008 |
| EP | 1414459 | 12/2009 |
| EP | 2135603 | 1/2013 |
| WO | 9852565 | 11/1998 |
| WO | 0003715 | 1/2000 |
| WO | 0135942 | 5/2001 |
| WO | 0226223 | 4/2002 |
| WO | 03013524 | 2/2003 |
| WO | 2005089486 | 9/2005 |
| WO | 2005112931 | 12/2005 |
| WO | 2007067341 | 6/2007 |
| WO | 2007100775 | 9/2007 |
| WO | 2007123865 | 11/2007 |
| WO | 2007137227 | 11/2007 |
| WO | 2008060381 | 5/2008 |
| WO | 2012104852 | 8/2012 |
| WO | 2012118562 | 9/2012 |

OTHER PUBLICATIONS

Buckholtz et al., "Dopaminergic Network Differences in Human Impulsivity," Science, vol. 329, p. 532, (Jul. 30, 2010).
Hollister et al., "Aversive Effects of Naltrexone in Subjects not Dependent on Opiates," Drug and Alcohol Dependence, vol. 8, pp. 37-41 (1981).
Mendelson et al., "Effects of Naltrexone on Mood and Neuroendocrine Function in Normal Adult Males," Psychoneuroendocrinology, vol. 3, pp. 231-236 (1979).
Singh, Vijay Pal et al., "Paradoxical effects of opioid antagonist naloxone on SSRI-induced analgesia and tolerance in mice," Pharmacology, vol. 69, No. 3, pp. 115-112 (Nov. 2003).
Balcells-Olivero, M. et al, "Naltrexone attenuates acute amphetamine-induced rearing and blocks its sensitization by repeated amphetamine," Society for Neuroscience Abstracts, vol. 22, No. 1-3, p. 78 (1996) Abstract.
Tiihonen et al. "A Comparison of Aripiprazole, Methylphenidate, and Placebo for Amphetamine Dependence" Am J Psychiatry 2007; 164:160-162. (3 pages).
Enz, Ralf. "The trick of the tail: protein-protein interactions of metabotrophic glutamate receptors" BioEssays 2006; 29:60-73. (14 pages).
Popowicz et al. "Filamins: promiscuous organizers of the cytoskeleton" TRENDS in Biochemical Sciences 2006; vol. 31(7). (9 pages).
Lin et al. "Dopamine D2 and D3 receptors are linked to the actin cytoskeleton via interaction with filamin A" PNAS 2001; 98(9): 5258-5263. <www.pnas.org/cgi/doi/10.1073/pnas.011538198> (6 pages).
Obadiah et al. "Adenylyl Cyclase Interaction with the D2 Dopamine Receptor Family; Differential Coupling to Gi, Gz and Gs" Cellular and Molecular Nuerobiology 1999; 19(5): 653-664. (12 pages).
Onoprishvili et al. "Interaction Between the u Opioid Receptor and Filamin A is Involved in Receptor Regulation and Trafficking" Mol Pharmacol 2003; 64(5): 1092-1100. (9 pages).
Seck et al. "Binding of Filamin to the C-terminal Tail of the Calcitonin Receptor Controls Recycling" The Journal of Biological Chemistry 2003; 278(12): 10408-10416. (9 pages).
Largent-Milnes et al. "Oxycodone Plus Ultra-Low-Dose Naltrexone Attenuates Neuropathic Pain and Associated u-Opioid Receptor-Gs Coupling" The Journal of Pain 2008; 9(8): 700-713. (14 pages).
Huang et al. "The calcium-sensing receptor and its interacting proteins" J. Cell. Mol. 2007; 11(5): 923-934. (12 pages).
Thomas et al. "G Protein Coupling and Signaling Pathway Activation by M Muscarinic Acetylcholine Receptor Orthosteric and Allosteric Agaonists" The Journal of Pharmacology and Experimental Therapeutics 2008; 327 (2):365-374. (10 pages).
Onoprishvili et al. "Chronic morphine treatment up-regulates mu opioid receptor binding in cells lacking Filamin A" Brain Res. 2007; 1177: 9-18. (20 pages).
Scott et al. "Cooperative Regulation of Extracellular Signal-Regulated Kinase Activation and Cell Shape Change by Filamin A B-Arrestins" Molecular and Cellular Biology 2006; 26(9): 3432-3445. (14 pages).
Paulus et al. "Less is more: pathophysiology of dopaminergic-therapy-related augmentation in restless legs syndrome" Lancet Neurol 2006, 5: 878-886. (9 pages).
Wang et al. "High-Affinity Naloxone Binding to Filamin A prevents Mu Opioid Receptor-Gs Coupling Underlying Opioid Tolerance and Dependence" PLoS One 2008; 3(2): e1554. <www.doi:10.137/journal.pone.0001554> (10 pages).
Bartlett et al. "Dopamine responsiveness is regulated by targeted sorting of D2 receptors" PNAS 2005; 102(32): 11521-11526. <www.pnas.org/cgi/doi/10.1073/pnas.0502418102> (6 pages).
Cho et al. "Roles of Protein Kinase C and Actin-Binding Protein 280 in the Regulation of Intracellular Trafficking of Dopamine D3 Receptor" Molecular Endocrinology; 21(9): 2242-2254. (13 pages).
Kim et al. "Differential Regulation of the Dopamine D2 and D3 Receptors by G Protein-coupled Receptor Kinases and B-Arrestins" The Journal of Biological Chemistry 2001; 276(40): 37409-37414. (6 pages).
Wang et al. "Naloxone's Pentapeptide Binding Site on Filamin A Blocks Mu Opioid Receptor-Gs Coupling and CREB Activation of Acute Morphine" PLoS One 2009; 4(1): e4282. <www.doi:10.137/journal.pone.0004282> (11 pages).
Kim et al. "G Protein-coupled Receptor Kinase Regulates Dopamine D3 Receptor Signaling by Modulating the Stability of a Receptor Filamin-B-Arrestin Complex" The Journal of Biological Chemistry 2005; 280(13): 12774-12780. (7 pages).
Scott et al. "Placebo and Nocebo Effects Are Defined by Opposite Opioid and Dopaminergic Responses" Arch Gen Psychiatry; 65(2): 220-231. (12 pages).
Lidstone et al. "Understanding the Placebo Effect: Contributions from Neuroimaging" Mol Imaging Biol 2007; 9: 176-185. (10 pages).
Besson et al. "Dopaminergic and Opioidergic Mediations of Tricyclic Antidepressants in the Learned Helplessness Paradigm" Pharmacology Biochemistry and Behaviour 1999; 64(3): 541-548. (8 pages).
Amiaz et al. "Resolution of treatment-refractory depression with naltrxone augmentation of paroxetine—a case report" Psychopharmacology 1999; 143: 433-434. (2 pages).
Carlezon et al. "Depressive-Like Effects of the k-Opioid Receptor Agonist Salvinorin A on Behavior and Neurochemistry in Rats" The Journal of Pharmacology and Experimental Therapeutics 2006; 316(1): 440-447. (8 pages).
Schug, Stephan A. "The role of tramadol in current treatment strategies for musculoskeletal pain" Therapeutics and Clinical Risk Management 2007; 3(5): 717-723. (7 pages).
Paquette et al. "Cannabinoid-included tolerance is associated with a CB1 receptor G protein coupling switch that is prevented by ultra-low does rimonabant" Behavioural Pharmacology 2007; 18: 767-776. (11 pages).
Tribal et al. "Apomorphine in idiopathic restless legs syndrome: an exploratory study" J Neurosurg Psychiatry 2005; 76(2): 181-185. (6 pages).
Farren et al., "Occurrence and Management of Depression in the Context of Naltrexone Treatment of Alcoholism," Am. J. Psychiatry 156:8, Aug. 1999, 1258-1262.
Burns, "Ultra-low-dose opioid antagonists enhance opioid analgesia while reducing tolerance, dependence and addictive properties," Recent Developments in Pain Research, 2005: 115-136, ISBN: 81-308-0012-8.
Younger et al., "The use of low-dose naltrexone (LDN) as a novel anti-inflammatory treatment for chronic pain," Clin Rheumatol, 2014, 33:451-459.

* cited by examiner

TREATMENTS FOR DEPRESSION AND OTHER DISEASES WITH A LOW DOSE AGENT

PRIORITY

The present application is a continuation-in-part of U.S. patent application Ser. No. 14/410,551, which, on Dec. 22, 2014, entered the U.S. National Stage of International Patent Application No. PCT/US2014/013874, filed Jan. 30, 2014, which claims priority to U.S. Provisional Application No. 61/758,551, filed on Jan. 30, 2013 and U.S. Provisional Application No. 61/814,476, filed on Apr. 22, 2013, the contents of which are herein incorporated by reference in their entireties. The present application is related to U.S. patent application Ser. No. 12/603,235, filed Oct. 21, 2009 and U.S. patent application Ser. No. 13/758,569, filed Feb. 4, 2013, the contents of which are incorporated by reference in their entireties.

FIELD OF THE INVENTION

The present invention relates to compositions and methods that are useful in treating various forms of depression and other disorders.

BACKGROUND

Mental illnesses and obesity are increasing prevalent disorders in the modern world and require improved treatments to maximize patient quality of life and reduce health care costs.

For instance, depression refers to a serious medical illness that affects one's thoughts, feelings, behavior, mood and physical health. Major depression, also referred to as clinical depression, major depressive illness, major affective disorder and unipolar mood disorder, may involve some combination of the following symptoms: depressed mood (sadness), poor concentration, insomnia, fatigue, appetite disturbances, excessive guilt and thoughts of suicide. Left untreated, depression can lead to serious impairment in daily functioning and even suicide. Suicide is the tenth leading cause of death in the U.S. Researchers believe that more than one-half of people who die by suicide are experiencing depression. Each year depression affects 5-8 percent of adults in the United States. Therefore, about 25 million Americans will have an episode of major depression this year alone. Without treatment, the frequency and severity of depression symptoms tend to increase over time.

Furthermore, attention deficit hyperactivity disorder (ADHD) is one of the most common childhood disorders and can continue through adolescence and adulthood. Symptoms include difficulty staying focused and paying attention, difficulty controlling behavior, and hyperactivity (over-activity). Parkinson's disease is a degenerative disorder of the central nervous system with marked motor symptoms linked, in part, to the death of dopamine-generating cells. Common symptoms of this disorder are movement-related, including shaking, rigidity, slowness of movement and difficulty with walking and gait. Behavioral problems and dementia are also common, particularly in late stage disease. Bipolar disorder describes a brain disorder that causes unusual shifts in mood, energy, activity levels, and the ability to carry out day-to-day tasks.

Obesity is a disorder marked by excessive body fat that negatively affects a patient's health. If a person's bodyweight is at least 20% higher than it should be, he or she is considered obese. Obesity is linked to a panoply of diseases, including coronary heart disease, type 2 diabetes, cancers (e.g., endometrial, breast, and colon), hypertension, dyslipidemia, stroke, liver and gallbladder disease, sleep apnea and respiratory problems, osteoarthritis, and gynecological problems, among others.

Unfortunately, sufficient treatment for these disorders has proven elusive. For instance, in the context of depression, while certain pharmaceuticals have proven somewhat successful, medical practitioners face the challenge of unpredictable responses and eventual loss of effect, necessitating constant evaluation of treatments and, often, changes in treatment regimens. Further, anti-depression pharmaceuticals are often characterized by unpleasant side effects.

Therefore, there remains a need for therapies that are useful for treating various mental illnesses and obesity.

BRIEF DESCRIPTION OF THE INVENTION

Accordingly, the present invention relates to improved compositions and methods for the treatment or prevention of various forms of depression and/or mood disorders, including, for example, breakthrough depression and treatment-refractory depression, and other mood disorders as well as other ADHD, Parkinson's disease, and obesity, among others.

In one aspect, the present invention provides a method of preventing or treating breakthrough depression in a patient in need thereof comprising administering an effective amount of low dose naltrexone or related opioid antagonist.

In another aspect, the present invention provides a method of preventing or treating treatment-refractory depression in a patient in need thereof comprising administering an effective amount of low dose naltrexone or related opioid antagonist.

In a further aspect, the present invention provides a method of preventing or treating breakthrough depression in a patient in need thereof comprising administering an effective amount of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (SSRI).

In another aspect, the present invention provides a method of preventing or treating treatment-refractory depression in a patient in need thereof comprising administering an effective amount of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (SSRI).

In another aspect, the present invention provides a method of preventing or treating one or more of depression, Parkinson's disease, attention deficit disorder (ADHD). Restless Leg Syndrome (RLS), and obesity comprising administering an effective amount of low dose naltrexone or related opioid antagonist in combination with an effective amount of another agent described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used

DETAILED DESCRIPTION OF THE INVENTION

Figure 1A:
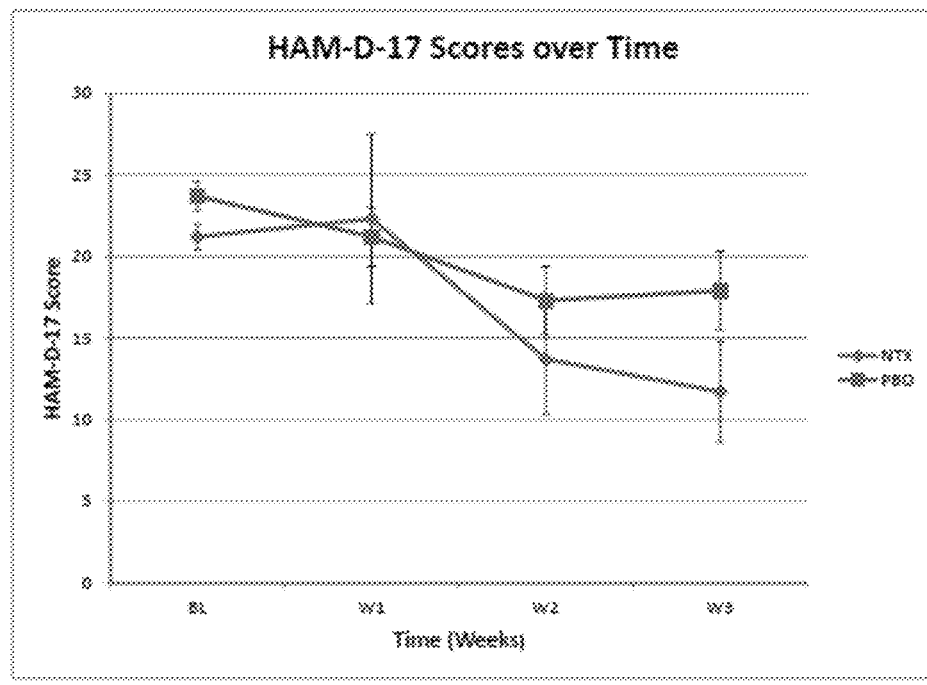
FIGS. 1A and 1B show patient response during clinical testing of low dose naltrexone treatment for depression as measured by 17-item Hamilton Rating Scale for Depression (HAM-D-17) over three weeks (FIG. 1A) and six weeks (FIG. 1B), respectively.

The present invention is based, in part, on the discovery that low dose naltrexone is useful in the treatment of various forms of depression and/or mood disorders, including, for example, breakthrough depression and treatment-refractory depression, and other mood disorders.

In one aspect, the present invention provides a method of preventing or treating breakthrough depression in a patient in need thereof comprising administering an effective amount of low dose naltrexone or related opioid antagonist. In one aspect, the present invention provides a use of low dose naltrexone or related opioid antagonist for the prevention or treatment of breakthrough depression.

In another aspect, the present invention provides a method of preventing or treating treatment-refractory depression in a patient in need thereof comprising administering an effective amount of low dose naltrexone or related opioid antagonist. In one aspect, the present invention provides a use of low dose naltrexone or related opioid antagonist for the prevention or treatment of treatment-refractory depression.

In a further aspect, the present invention provides a method of preventing or treating breakthrough depression in a patient in need thereof comprising administering an effective amount of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (SSRI). In one aspect, the present invention provides a use of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (SSRI) for the prevention or treatment of breakthrough depression.

In another aspect, the present invention provides a method of preventing or treating treatment-refractory depression in a patient in need thereof comprising administering an effective amount of low dose naltrexone or related opioid antagonist in combination with an effective amount of one or more of a dopamine active anti-depressant agent, a dopamine active augmenting agent, a serotonin-norepinephrine reuptake inhibitor (SNRT), and a selective serotonin re-uptake inhibitor (SSRI). In one aspect, the present invention provides a use of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (SSRI) for the prevention or treatment of treatment-refractory depression.

In another aspect, the present invention provides a method of preventing or treating one or more of depression, Parkinson's disease, bipolar disorder, bipolar mood disorder, attention deficit disorder (ADHD), Restless Leg Syndrome (RLS), and obesity comprising administering an effective amount of low dose naltrexone or related opioid antagonist optionally in combination with an effective amount of another agent described herein. In another aspect, the present invention provides a use of low dose naltrexone or related opioid antagonist optionally in combination another agent described herein for the prevention or treatment of one or more of depression, Parkinson's disease, bipolar disorder, bipolar mood disorder, attention deficit disorder (ADHD), Restless Leg Syndrome (RLS), and obesity.

In one embodiment, the effective amount of low dose naltrexone or related opioid antagonist or a combination of an effective amount of low dose naltrexone or related opioid antagonist in combination with an effective amount of an agent described herein is administered in conjunction with a patient's pre-existent anti-depression treatment, wherein the pre-existent anti-depression treatment comprises one or more of a dopamine active anti-depressant agent, a dopamine active augmenting agent, a serotonin-norepinephrine reuptake inhibitor (SNRT), and a selective serotonin re-uptake inhibitor (SSRI). In one embodiment, the presently described methods of treatment involve the administration of an effective amount of low dose naltrexone or related opioid antagonist in combination with an effective amount of an agent described herein. In one embodiment, the presently described methods of treatment involve the administration of an effective amount of low dose naltrexone or related opioid antagonist to a patient undergoing treatment with an effective amount of an agent described herein. In some embodiments, the effective amount of low dose naltrexone or related opioid antagonist is an adjuvant therapy to another agent described herein.

In another embodiment, the breakthrough depression comprises depressive relapse and/or recurrence.

In still another embodiment, the low dose naltrexone or related opioid antagonist is administered at doses that reverse or prevent desensitization of a dopamine receptor, including, for example, the $D_2$ and $D_3$ receptors. In still another embodiment, the low dose naltrexone or related opioid antagonist is administered at doses that do not effect opioid receptors. In still another embodiment, the low dose naltrexone or related opioid antagonist is administered at doses that are substantially below levels that induce significant opioid blockade.

Substantially below refers to levels are less than about 50%, or about 40%, or about 30%, or about 20%, or about 10%, or about 5%, or about 2%, or about 1% of levels that induce significant opioid blockade. In one embodiment, the amount of naltrexone or related opioid antagonist administered is less than 10 mg, or about 1 to about 4 mg, or about 1 mg.

In another embodiment, the dopamine active anti-depressant agent is one or more of bupropion, aripiprazole, and sertraline. In some embodiments, aripiprazole is not an anti-depressant agent per se. In another embodiment, the SNRT is selected from duloxetine, venlafaxine, nefazodone, and milnacipran. In another embodiment, the dopamine active augmenting agent is one or more of an amphetamine salt, pramipexole, and ropinirole. In another embodiment, the SSRI is selected from citalopram, dapoxetine, s-citalopram, fluoxetine, fluvoxamine, indalpine, paroxetine, and zimelidine.

In various embodiments, the preventing or treating of depression, including, breakthrough depression and/or treatment-refractory depression, comprises reduction in length of a depressive episode. In various embodiments, the preventing or treating of depression, including, breakthrough depression and/or treatment-refractory depression, comprises recovery of an anti-depressive effect of the patient's pre-existent anti-depression treatment regimen. In still other various embodiments, the preventing or treating of depression, including, breakthrough depression and/or treatment-refractory depression, comprises a reduction in the rate of relapse after major depressive episodes. In further various embodiments, the preventing or treating of depression, including, breakthrough depression and/or treatment-refractory depression, comprises prevention or reversal of loss of efficacy of the patient's pre-existent anti-depression treatment. In various embodiments, the preventing or treating of depression, including, breakthrough depression and/or treatment-refractory depression, comprises reduction in an effective dosage of the patient's pre-existent anti-depression treatment, which may, for example, causes one or more of a reduction in side effects and increase in patient adherence. In some embodiments, the depression being treated is bipolar depression. Including, for example, treatment resistant bipolar depression.

In another embodiment, the effective amount of low dose naltrexone or related opioid antagonist or a combination regimen comprising naltrexone or related opioid antagonist is administered orally or subcutaneously.

In still another embodiment, the naltrexone or related opioid antagonist and one or more of a dopamine active anti-depressant agent, a dopamine active augmenting agent, a serotonin-norepinephrine reuptake inhibitor (SNRT), and a selective serotonin re-uptake inhibitor (SSRI) are co-formulated in a single dosage form. In various embodiments, the dosage form is an oral dosage form or a subcutaneous dosage form.

In still another embodiment, an outcome of the methods of the present invention is rapid antidepressant response (e.g. less than about 10 days) compared to the usual latency for response to traditional antidepressant pharmacotherapy (about 3-6 weeks).

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount" of a "therapeutically effective amount," when used in connection with medical uses is an amount that is effective for providing a measurable treatment, prevention, or reduction in the rate of pathogenesis of a disease of interest.

Effective amounts, toxicity, and therapeutic efficacy can be determined by standard pharmaceutical procedures in, for example, cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are provided. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

In certain embodiments, a pharmacologically effective amount that will treat the disease recited herein will modulate the symptoms typically by at least about 10%, at least about 20%, at least about 30%, at least about 40%, or at least about 50%.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

In various aspects, the present invention pertains to various forms of depression and other mood disorders. Diagnosis of depressive conditions may be informed by criteria found in the American Psychiatric Association's revised fourth edition of the *Diagnostic and Statistical Manual of Mental Disorders* (DSM-IV-TR), and the World Health Organization's *International Statistical Classification of Diseases and Related Health Problems* (ICD-10). Generally, depressive episode refers to a single episode and recurrent depressive disorder refers to repeated episodes. Both DSM-IV-TR and ICD-10 mark out typical depressive symptoms. ICD-10 defines three typical depressive symptoms, depressed mood, anhedonia, and reduced energy. Two of these should be present to determine depressive disorder diagnosis. DSM-IV-TR defines two main depressive symptoms, depressed mood and anhedonia. At least one of these must be present to make a diagnosis of a major depressive episode.

Depression encompasses a large variety of disorders, including, but not limited to, the five further subtypes of major depressive disorder (MDD), i.e. melancholic depression, atypical depression, catatonic depression, postpartum depression, and seasonal affective disorder. In some embodiments, the depression is dopamine-receptor related depression. In some embodiments, the present depression is not related to opioid receptors.

The present invention, in some aspects, pertains to depression and mood disorders that are described and classified by the DSM codes. These can include, for example: major depressive disorder, recurrent—296.36, in full remission—296.35, in partial remission—296.31, mild—296.32, moderate—296.33, severe without psychotic features—296.34, severe with psychotic features—296.30, unspecified, as well as major depressive disorder, single episode—296.26, in full remission—296.25, in partial remission—296.21, mild—296.22, moderate—296.23, severe without psychotic features—296.24, severe with psychotic features—296.20, unspecified, as well as 311 depressive disorder, not otherwise specified (NOS). Further, codes 293.83—mood disorder due to . . . [general medical condition] and 296.90—mood disorder NOS, are included.

The present invention includes compositions and methods for the treatment and/or prevention of the various disorders encompassed in the term depression, and related mood disorders.

Breakthrough depression is a subset of depression that may be caused by tachyphylaxis or antidepressant tolerance, often called antidepressant "poop-out." Breakthrough depression is often characterized as a condition in which patients experience a good initial antidepressant response which is lost over time with repeated or prolonged antidepressant treatment. This phenomenon is distinct from an initial non-response or a partial response. In one embodiment, the breakthrough depression comprises depressive relapse and/or recurrence.

Treatment-resistant depression is a subset of depression that is often characterized as a condition in which optimization of treatment or complete remission does not occur. When remission is not achieved, the probability of relapse is greater. In one embodiment, the treatment-resistant depression comprises depressive relapse and/or recurrence.

Further, in some aspects, the present invention comprises treatment of other disorders individually or in combination with depression as described herein. For example, in some embodiments, the present invention includes the treatment of one or more of depression, Parkinson's disease, bipolar disorder, bipolar mood disorder, attention deficit disorder (ADHD), Restless Leg Syndrome (RLS), and obesity. In some embodiments, the present invention is useful for treatment of one or more of depression, Parkinson's disease, bipolar disorder, bipolar mood disorder, ADHD, RLS, and obesity in the same subject.

In some embodiments, the present invention includes treatment of Parkinson's disease. Parkinson's disease occurs when a group of cells in the substantia nigra that produce dopamine malfunction and die. When a subject has Parkinson's disease, his or her dopamine-producing cells begin to die, and therefore, the amount of dopamine produced in the brain decreases. Signals from the brain that tell the body how and when to move are therefore delivered more slowly, leaving a subject incapable of initiating and controlling movements in a normal way. Four symptoms of Parkinson's disease are tremor, or trembling in hands, arms, legs, jaw, and face; rigidity, or stiffness of the limbs and trunk; bradykinesia, or slowness of movement; and postural instability, or impaired balance and coordination. Other symptoms may include depression and other emotional changes; difficulty in swallowing, chewing, and speaking; urinary problems or constipation; skin problems; and sleep disruptions, etc. Accordingly, the methods and compositions of the present invention are useful for treatment of Parkinson's disease. In some embodiments, the present invention is useful for treatment of both Parkinson's disease and depression in the same subject.

In some embodiments, the present compositions and methods are useful in the treatment of Parkinson's disease and/or depression, including by way of non-limiting example, breakthrough depression and/or treatment-refractory depression, associated with and/or caused by Parkinson's disease. In some embodiments, the present invention provides a method for treating Parkinson's disease and/or depression, including by way of non-limiting example, breakthrough depression and/or treatment-refractory depression, associated with and/or caused by Parkinson's disease by administering an effective amount of a low dose naltrexone to a patient in need thereof. The patient may also receive pre-existent and/or combination therapy that comprises one or more of the agents described herein.

In some embodiments, the present invention includes treatment of bipolar disorder and/or bipolar mood disorder. Bipolar disorder is in a class of mood disorders that is marked by dramatic changes in mood, energy and behavior. A key characteristic of people with bipolar disorder is alternating between episodes of mania (extreme elevated mood) and depression (extreme sadness). These episodes can last from hours to months. The mood disturbances are severe enough to affect the person's ability to function. The experience of mania can be very frightening and lead to impulsive behavior that has serious consequences for the person and the family. A depressive episode makes it difficult or impossible for a person to function in his or her daily life. Symptoms of depression include, for example, sad mood; preoccupation with failures or inadequacies; loss of self-esteem; slowed thinking, forgetfulness; difficulties in concentrating and in making decisions; loss of interest in work, hobbies, people; social isolation; lethargy or agitation; changes in appetite; oversleeping or insomnia; decreased sexual drive; and suicidal thoughts. Symptoms of mania include, for example, elevated, expansive mood; extreme irritability; rapid, unpredictable emotional changes; racing thoughts, flights of ideas; overreaction to stimuli; misinterpretation of events; increased interest in activities; overspending; sense of grandiosity, inflated self-esteem; excessive energy; decreased need for sleep; increased sexual drive, sexual indiscretions; and poor judgment.

In some embodiments, the present compositions and methods are useful in the treatment of depression, including by way of non-limiting example, breakthrough depression and/or treatment-refractory depression, associated with and/or caused by bipolar disorder and/or bipolar mood disorder. In some embodiments, the present invention provides a method for treating depression, including by way of non-limiting example, breakthrough depression and/or treatment-refractory depression, associated with and/or caused by bipolar disorder and/or bipolar mood disorder by administering an effective amount of a low dose naltrexone to a patient in need thereof. The patient may also receive pre-existent and/or combination therapy that comprises one or more of the agents described herein. In some embodiments, the pre-existent and/or combination therapy is bupropion. In various embodiments, depression, including by way of non-limiting example, breakthrough depression and/or treatment-refractory depression, associated with and/or caused by bipolar disorder and/or bipolar mood disorder is distinct from unipolar depression, including by way of non-limiting example, breakthrough depression and/or treatment-refractory depression.

In some embodiments, the present invention includes treatment of ADHD. ADHD is a disorder characterized by, for example, inattentiveness, over-activity, impulsivity, or a combination. Decreased phasic dopamine release is believed, without wishing to be bound by theory, to be an important deficit in ADHD. Accordingly, the methods and compositions of the present invention are useful for treatment of ADHD. In some embodiments, the present invention is useful for treatment of both ADHD and depression in the same subject.

In the treatment of ADHD, exemplary agents for coformulation include, but are not limited to, a methylphenidate formulation (e.g. in immediate or delayed release form, including selective enantiomers), an amphetamine formulation (e.g. in an immediate or delayed release form, including selective enantiomers), or a norepinephrine transporter inhibitor such as atomoxetine, all of whose actions are believed, without wishing to be bound by theory, to be mediated by augmentation of extracellular dopamine levels, as well as other drugs enhancing dopaminergic neurotransmission. Typical doses of ADDERALL, an amphetamine preparation, range from a daily dose of 2.5 mg per day up to doses 30 mg given twice a day orally. Typical doses of CONCERTA range from 18 mg/day to 72 mg/day, generally not to exceed 2 mg/kg/day. Typical doses of RITALIN (methylphenidate) tablets are 10 to 60 mg/day given twice or three times per day; higher doses have been used. Typical doses of atomoxetine are 0.5 mg/kg to 1.4 mg/kg taken twice daily orally up to a maximum of a 100 mg daily dose. Lower doses may be effective, when co-administered or co-formulated with a low dose of naltrexone, naloxone, or other opioid receptor antagonist. A benefit of low dose opioid antagonists stabilizing dopamine augmentation in treatment of ADHD includes the prevention of dose escalation, therefore allowing use of lower doses of agents such as amphetamine salts and methylphenidate, which would, without wishing to be bound by theory, minimize the known cardiovascular risks of arrhythmias, hypertension and and/or tachycardia linked to an elevated lifetime probability of myocardial infarction and stroke. In some embodiments, the present methods and formulations pertain to methylphenidate along with d-amphetamine.

In some embodiments, the present invention provides a method for treating ADHD by administering an effective amount of a low dose naltrexone to a patient in need thereof. The patient may also receive pre-existent and/or combination therapy that comprises one or more of the agents described herein.

In some embodiments, the present invention includes treatment of RLS, also known as Willis-Ekbom disease (WED). RLS is a disorder of the part of the nervous system that affects the legs and causes an urge to move them. Because it can interfere with sleep, it may be considered a sleep disorder. RLS is a neurological disorder characterized by an irresistible urge to move one's body to stop uncomfortable or odd sensations. It most commonly affects the legs, but can affect the arms, torso, head, and even phantom limbs. Moving the affected body part modulates the sensations, providing temporary relief. In some embodiments, the present invention includes treatment or prevention of RLS comprising administering low dose naltrexone (or other opioid receptor antagonist), optionally in combination with any of the agents described herein.

In some embodiments, the present invention provides a method for treating RLS by administering an effective amount of a low dose naltrexone to a patient in need thereof. The patient may also receive pre-existent and/or combination therapy that comprises one or more of the agents described herein.

In some embodiments, the present invention includes treatment of obesity and metabolic syndrome which may accompany obesity, including, by way of non-limiting example, insulin resistance and type II diabetes. Bromocriptine, a dopamimetic, at a dose of 2.5 mg reduces leptin, insulin, and glucose levels in obese female human subjects and improves glycemic control in type II diabetics. Genetic studies have shown genetic polymorphisms of the dopamine D3 receptor which produce lesser levels of dopamine D3 signaling are more commonly seen in obese adults particularly those with binge eating disorders. Further, imaging studies have suggested that decreased dopamine D2 signaling in obese subjects and animal studies have shown that bromocriptine administered to leptin deficient animals reduces hyperphagia and adiposity. In some embodiments, low dose naltrexone (or other opioid receptor antagonist), optionally in combination with any of the agents described herein, including dopamine D2 and D3 agonists and partial agonists including but not limited to bromocriptine, are useful in the treatment of obesity and metabolic syndrome which may accompany obesity. Without wishing to be bound by theory, such treatment may enhance the metabolic effects of such dopamimetics by preventing desensitization of dopamine D2 and D3 receptors with chronic treatment. In some embodiments, the present invention is useful for treatment of both obesity and metabolic syndrome which may accompany obesity and depression in the same subject.

In some embodiments, the present invention provides a method for treating obesity and/or metabolic syndrome which may accompany obesity, including, by way of non-limiting example, insulin resistance and type II diabetes by administering an effective amount of a low dose naltrexone to a patient in need thereof. The patient may also receive pre-existent and/or combination therapy that comprises one or more of the agents described herein. In some embodiments, the present invention provides a method for treating binge eating disorder, including moderate to severe binge eating disorder. In various embodiments, the treatment of binge eating disorder may include a combination therapy of low dose naltrexone and lisdexamfetamine (e.g. VYVANSE).

Naltrexone (17-(cyclopropylmethyl)-4,5α-epoxy-3,14-dihydroxymorphinan-6-one) is a small molecule agent of the following structure:

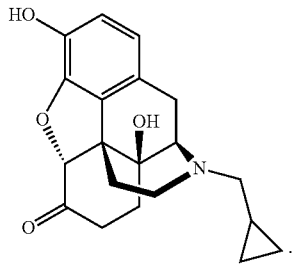

Naltrexone is a potent, orally bioavailable opioid receptor antagonist. More specifically, without wishing to be bound by theory, naltrexone is a competitive antagonist (possibly exerting inverse agonistic effects) at mu and delta opioid receptors. It has been used clinically in the management of alcohol dependence and in the treatment of opioid dependence. In the context of alcohol dependence, naltrexone was approved by the U.S. F.D.A. in 1994. Since then a number of studies have confirmed its efficacy in reducing frequency and severity of relapse to drinking. The standard regimen is one 50 mg tablet per day, when administered orally or 380 mg every 4 weeks (or once a month) via intramuscular gluteal injection, alternating buttocks for an extended-release injectable suspension (e.g. VIVITROL). In the context of opioid dependence, naltrexone was approved by the U.S. F.D.A. in 1984. Naltrexone may help patients overcome opioid addiction by blocking the drugs' euphoric effects. The standard regimen is an initial dose of 25 mg orally one time and maintenance doses of, if no withdrawal signs occur, 50 mg orally once a day, or as alternatives (e.g. to improve compliance): 50 mg orally on week days and 100 mg orally on Saturday; or 100 mg orally every other day; or 150 mg orally every third day, when administered orally or 380 mg every 4 weeks (or once a month) via intramuscular gluteal injection, alternating buttocks for an extended-release injectable suspension.

A significant disadvantage of the prescription of an opioid antagonist, such as naltrexone and related opioid antagonists, at a usual dose is that they render a patient inaccessible to opioid analgesia in emergency situations. Another major limitation of the usual does of naltrexone and related opioid antagonists is that these doses of naltrexone and related opioid antagonists or inverse agonists carry a risk of hepatotoxicity. Further, opioid blocking doses of naltrexone and related opioid antagonists, perhaps because of their inverse agonist effect, can create dysphoria and/or possible anhedonia. This could exacerbate depression and/or promote suicidal ideation (as noted by the FDA in their warnings accompanying usual doses of naltrexone either p.o. or s.c).

Surprisingly, low dose naltrexone (e.g. less than 10 mg) was found to enhance the effects of opioid agonists. As a possible mechanism of action, without wishing to be bound by theory, recent studies determined that naltrexone binds to the C-terminal pentapeptide of the scaffolding protein filamin A (which is involved in receptor trafficking) with strong avidity ($K_D$ less than 5 pM), which may prevent or reverse a change in G-protein signaling in G coupled receptor systems, such as the mu opioid receptor, after prolonged stimulation by agonists (Wang, Frankfurt, & Burns, 2008 PloS One, 3(2), e1554). Filamin A is also found in Dopamine 2 and 3 receptors.

Accordingly, in some aspects of the invention there are provided compositions and methods comprising low dose naltrexone or a related opioid antagonist that reverse or prevent desensitization to $D_2/D_3$ agonists. Accordingly, in some aspects of the invention there are provided compositions and methods comprising low dose naltrexone or a related opioid antagonist that do not effect opioid receptors. In studies regarding the illness Restless Leg Syndrome (RLS), thought to result from a deficiency of $D_2/D_3$ compared to $D_1$ agonism, and typically treated with the $D_2/D_3$ agonists pramipexole or ropinirole, periodic limb movements of sleep were measured with Philips Respironics Actigraphy devices, confirming that low dose naltrexone allowed equivalent control of limb movements at one-half the prior dose of $D_2/D_3$ agonists (see U.S. Ser. No. 12/603,235, hereby incorporated by reference in its entirety).

Additionally, there have been reported observations that following successful treatment of depression with SSRIs, a $D_2$ antagonist brought return of depressive symptoms (Wilner et al., 2005, J. Affective Disorders, 86(1), 37-45, the contents of which are hereby incorporated by reference in its entirety). Analogous observations in an animal model of depression, reversed by tricyclic antidepressants, suggested that retention of sensitivity of the $D_2$ receptor (i.e., preventing its desensitization) was essential to effective antidepressant treatments with SSRIs or SNRIs (Wilner, 2002 in Di Chiara, G. (Ed.) Handbook of Physiology: Dopamine in the CNS. Springer, Berlin, pp. 387-416, the contents of which are hereby incorporated by reference in its entirety).

Further, in Parkinson's Disease, dopamine D2 and/or D2/3 agonists, monoamine oxidase inhibitors (MAOi), catechol-O-methyl transferase inhibitors (COMTi), and L-DOPA formulations, either separately or together have been shown to be therapeutically efficacious. The dopamine D2 and D2/3 agonists include, but are not limited, to pramipexole, ropinirole, bromocriptine, sumanirole, and pergolide. The side effects of "wearing off" and "on-off" periods, as well as loss of therapeutic efficacy of these agents, have been reported with these drugs. Without wishing to be bound by theory, these effects may be mediated by desensitization of dopamine D2 and D3 receptors.

Accordingly, in various aspects, the present invention pertains to doses of naltrexone or related opioid antagonist that reverse or prevent desensitization of a dopamine receptor, including, for example, the $D_2$ and $D_3$ receptors. In other embodiments, any dopamine receptor of the $D_1$-like family and/or $D_2$-like family is the dopamine receptor on which doses of naltrexone or related opioid antagonist reverse or prevent desensitization. In some embodiments, the dopamine receptor is any one of the $D_1$, $D_2$, $D_3$, $D_4$, and $D_5$ receptors. In various aspects, the present invention pertains to doses of naltrexone or related opioid antagonist that are substantially below levels that induce significant opioid blockade.

In various aspects, the present invention also encompasses compositions and methods of treatment comprising other opioid antagonists related to naltrexone. These compounds include, by way of non-limiting example, naloxone, diprenorphine, etorphine, dihydroetorphine, and combinations thereof.

In one embodiment, the amount of naltrexone or related opioid antagonist administered is less than 10 mg. In another embodiment, amount of naltrexone or related opioid antagonist administered is about 9 mg, or about 8 mg, or about 7 mg, or about 6 mg, or about 5 mg, or about 4 mg, or about 3 mg, or about 2 mg, or about 1 mg. In some embodiments, the dose of naltrexone or related opioid antagonist is less than 1 mg. In a specific embodiment, the dose of naltrexone or related opioid antagonist is 1 mg. In some embodiments, the amount of naltrexone or related opioid antagonist administered is 1 mg or greater up to and not including 5 mg. In some embodiments, the amount of naltrexone or related opioid antagonist administered is 1 mg or greater, but no greater than 5 mg, or about 4 mg, or about 3 mg, or about 2 mg. In an illustrative embodiment, the naltrexone or related opioid antagonist is administered orally is 1 mg or greater up to and not including 5 mg. In some embodiments, the naltrexone or related opioid antagonist is not provided for bolus administration.

In some embodiments, the naltrexone or related opioid antagonist is dosed monthly, or weekly, or daily, or twice daily. In a specific embodiment, the dose is twice daily (i.e. bid).

In various embodiments, the naltrexone or related opioid antagonist is administered at about 9, or about 8, or about 7, or about 6, or about 5, or about 4, or about 3, or about 2, or about 1 mg bid. In a specific embodiment, the dosing is 1 mg bid.

In various embodiments, the present invention provides for the co-administration and/or co-formulation of low dose naltrexone or related opioid antagonist and one or more additional agents. Further, in some embodiments, the invention provides administration of low dose naltrexone or related opioid antagonist in the context of pre-existent treatments (e.g. anti-depression treatments) that comprise one or more additional agents.

In some embodiments the present invention provides the methods and compositions that comprise dopamine active anti-depressant agent.

Dopamine active anti-depressant agents include agents that effect dopamine levels.

In some embodiments, the dopamine active anti-depressant agent is one or more of bupropion, aripiprazole, brexpiprazole, and sertraline.

Bupropion ((±)-2-(tert-Butylamino)-1-(3-chlorophenyl) propan-1-one), without wishing to be bound by theory, may have its primary pharmacological action through norepinephrine-dopamine reuptake inhibition. It binds selectively to the dopamine transporter, but its behavioral effects may be attributed to its inhibition of norepinephrine reuptake. It also may act as a nicotinic acetylcholine receptor antagonist.

Aripiprazole (7-{4-[4-(2,3-Dichlorophenyl)piperazin-1-yl]butoxy}-3,4-dihydroquinolin-2(1H)-one) and brexpiprazole (7-{4-[4-(1-benzothiophen-4-yl)piperazin-1-yl] butoxy}quinolin-2(1H)-one)), without wishing to be bound by theory, are partial dopamine agonist of the second generation class of atypical antipsychotics with additional antidepressant properties that is used in the treatment of schizophrenia, bipolar disorder, and clinical depression. It is approved by the U.S. FDA and EMA for various uses. Without wishing to be bound by theory, Aripiprazole is a dopamimetic at low doses; for example, below 10 mg, or below 9 mg, or below 8 mg, or below 7 mg, or below 6 mg, or below 5 mg, or below 4 mg, or below 3 mg, or below 2 mg, or below 1 mg. In some embodiments, the present invention comprises methods of treatment and compositions comprising low dose naltrexone or related opioid antagonist and aripiprazole. In some embodiments, aripiprazole may be considered to be an anti-depressant agent. In some embodiments, aripiprazole is not an anti-depressant agent.

Sertraline ((1S,4S)-4-(3,4-dichlorophenyl)-N-methyl-1,2,3,4-tetrahydronaphthalen-1-amine) is a compound of various mood disorder mechanisms. Without wishing to be bound by theory, it may be a dopamine active antidepressant; for example, at doses of 150 mg or above (for example, 160, or 170, or 180, or 190, or 200 mg). Without wishing to be bound by theory, it may also be an antidepressant of the selective serotonin reuptake inhibitor (SSRI) class. It is approved by the U.S. FDA. In some embodiments, the present invention provides methods and compositions comprising doses of sertraline at doses at which sertraline acts as an inhibitor of dopamine uptake. For example, the present invention encompasses doses of sertraline of doses of above 150 mg daily or above 200 mg daily or above 250 mg daily. In some embodiments, the present invention relates to a method of treating depression, including by way of non-limiting example, breakthrough depression and/or treatment-refractory depression, comprising administering a therapeutically effective low dose amount of naltrexone to a patient receiving doses of sertraline of doses of above 150 mg daily. In some embodiments, the present invention relates to a method of treating depression, including by way of non-limiting example, breakthrough depression and/or treatment-refractory depression, comprising administering a therapeutically effective low dose amount of naltrexone to a patient receiving doses of sertraline of doses of above 150 mg daily as a combination therapy. In some embodiments, the therapeutically effective low dose amount of naltrexone is 1 mg, optionally bid.

In some embodiments, the present invention provides methods and compositions that comprise serotonin-norepinephrine reuptake inhibitors (SNRIs).

SNRIs include agents which act upon, and increase, the levels of the neurotransmitters serotonin and norepinephrine, which play an important role in mood.

In some embodiments, the SNRI is one or more of duloxetine ((+)-(S)—N-Methyl-3-(naphthalen-1-yloxy)-3-(thiophen-2-yl)propan-1-amine), venlafaxine ((RS)-1-[2-dimethylamino-1-(4-methoxyphenyl)-ethyl]cyclohexanol), nefazodone (1-(3-[4-(3-chlorophenyl)piperazin-1-yl]propyl)-3-ethyl-4-(2-phenoxyethyl)-1H-1,2,4-triazol-5(4H)-one), and milnacipran ((1R*,2S*)-2-(aminomethyl)-N,N-diethyl-1-phenylcyclopropanecarboxamide). These agents are approved by the U.S. FDA for various uses. For example, the present invention encompasses doses of duloxetine of doses of above 60 mg daily or above 80 mg daily or above 100 mg daily. In some embodiments, the present invention relates to a method of treating depression, including by way of non-limiting example, breakthrough depression and/or treatment-refractory depression, comprising administering a therapeutically effective low dose amount of naltrexone to a patient receiving doses of duloxetine of doses of above 80 mg daily. In some embodiments, the present invention relates to a method of treating depression, including by way of non-limiting example, breakthrough depression and/or treatment-refractory depression, comprising administering a therapeutically effective low dose amount of naltrexone to a patient receiving doses of duloxetine of doses of above 80 mg daily as a combination therapy. In some embodiments, the therapeutically effective low dose amount of naltrexone is 1 mg bid.

Further, SNRIs are also provided in certain embodiments, including, for example, desvenlafaxine, tramadol, and sibutramine.

In some embodiments the present invention provides the methods and compositions that comprise dopamine active augmenting agents.

In some embodiments dopamine active augmenting agents include agents that may be used in the treatment of depression or other mood disorders and which have been shown to boost the antidepressant effect of a main antidepressant treatment.

In some embodiments, the dopamine active augmenting agent is one or more of an amphetamine salt, pramipexole, and ropinirole.

Amphetamine salts include, for example, ADDERALL, a combination of four amphetamine salts (racemic amphetamine aspartate monohydrate, racemic amphetamine sulfate, dextroamphetamine saccharide, and dextroamphetamine sulfate). ADDERALL, without wishing to be bound by theory, is a dopamine releasing agent, a norepinephrine releasing agent, and can be mildly serotonergic.

Pramipexole ((S)—$N^6$-propyl-4,5,6,7-tetrahydro-1,3-benzothiazole-2,6-diamine)), without wishing to be bound by theory, is a dopamine agonist of the non-ergoline class.

Ropinirole (4-[2-(dipropylamino)ethyl]-1,3-dihydro-2H-indol-2-one)), without wishing to be bound by theory, is also a dopamine agonist of the non-ergoline class of medications.

In some embodiments, the present invention provides the methods and compositions that comprise selective serotonin re-uptake inhibitors (SSRIs).

SSRIs include agents which act upon, and increase, the levels of the neurotransmitter serotonin, which plays an important role in mood.

In some embodiments, the SSRI is one or more of citalopram ((RS)-1-[3-(dimethylamino)propyl]-1-(4-fluorophenyl)-1,3-dihydroisobenzofuran-5-carbonitrile), Dapoxetine (S)—N,N-dimethyl-3-(naphthalen-1-yloxy)-1-phenylpropan-1-amine), S-Citalopram ((S)-1-[3-(dimethylamino)propyl]-1-(4-fluorophenyl)-1,3-dihydroisobenzofuran-5-carbonitrile), Fluoxetine ((RS)—N-methyl-3-phenyl-3-[4-(trifluoromethyl)phenoxy]propan-1-amine), Fluvoxamine ((E)-5-methoxy-1-[4-(trifluoromethyl)phenyl]pentan-1-one O-2-aminoethyl oxime), Indalpine (3-(2-piperidin-4-yl-ethyl)-1H-indole), Paroxetine ((3S,4R)-3-[(2H-1,3-benzodioxol-5-yloxy)methyl]-4-(4-fluorophenyl)piperidine), and Zimelidine ((Z)-3-(4-bromophenyl)-N,N-dimethyl-3-(pyridin-3-yl)prop-2-en-1-amine).

Further SSRIs are also provided in certain embodiments, including, for example, citalopram, escitalopram, paroxetine, fluoxetine, and fluvoxamine.

In various other embodiments, the invention provides further agents that may be used in the methods and compositions described herein.

For example, in some embodiments, further agents may include serotonin antagonist and reuptake inhibitors (SARIs), such as, for example, etoperidone, lubazodone, nefazodone, and trazodone.

In other embodiments further agents may include norepinephrine reuptake inhibitors (NRIs), such as, for example, atomoxetine, reboxetine, and viloxazine.

In still other embodiments, further agents may include norepinephrine-dopamine reuptake inhibitors (NDRIs), such as, for example, bupropion, dexmethylphenidate, methylphenidate, and methylphenidate. In some embodiments, the present invention comprises methods of treatment and compositions comprising low dose naltrexone or related opioid antagonist and methylphenidate.

In other embodiments, further agents may include norepinephrine-dopamine releasing agents (NDRAs), such as, for example, amphetamine, various amphetamine salts (e.g. salts of racemic amphetamine and dextroamphetamine, Adderall), dextroamphetamine, dextromethamphetamine, lysine-amphetamine (e.g. Vyvanase) and lisdexamfetamine. In some embodiments, the present invention comprises methods of treatment and compositions comprising low dose naltrexone or related opioid antagonist and amphetamines.

In yet another embodiment, further agents may include tricyclic antidepressants (TCAs), such as, for example, amitriptyline, butriptyline, clomipramine, desipramine, dosulepin, doxepin, imipramine, iprindole, lofepramine, melitracen, nortriptyline, opipramol, protriptyline, and trimipramine.

In yet another embodiment, further agents may include tetracyclic antidepressants (TeCAs), such as, for example, amoxapine, maprotiline, mianseri, and mirtazapine.

In other embodiments, further agents may include monoamine oxidase inhibitors (MAOIs), such as, for example, isocarboxazid, moclobemide, phenelzine, pirlindole, selegiline, and tranylcypromine.

In other embodiments further agents may include 5-$HT_{1A}$ receptor partial agonists, such as, for example, buspirone, tandospirone, aripiprazole, vilazodone, and quetiapine.

In still other embodiments further agents may include 5-$HT_2$ receptor partial agonists, such as, for example, aripiprazole.

In yet another embodiment, further agents may include 5-$HT_2$ receptor antagonists, such as, for example, agomelatine, nefazodone, quetiapine, and trimipramine.

In other embodiments further agents may include 5-$HT_7$ receptor antagonists, such as, for example, aripiprazole and quetiapine.

In other embodiments further agents may include $D_2$ receptor partial agonists, such as, for example, aripiprazole.

In still other embodiments further agents may include $D_2$ receptor antagonists, such as, for example, quetiapine.

In other embodiments further agents may include $D_3$ receptor antagonists, such as, for example, aripiprazole.

In other embodiments further agents may include $D_4$ receptor antagonists, such as, for example, aripiprazole.

In other embodiments agents may include α-adrenergic receptor antagonists, such as, for example, aripiprazole, mirtazepine, and quetiapine. Mirtazapine (REMERON, AVANZA, ZISPIN) is a noradrenergic and specific serotonergic antidepressant (NaSSA) useful for the treatment of depression. It may be classified, without wishing to be bound by theory, as a centrally acting $α_2$-adrenergic receptor antagonist. In some embodiments, the present invention comprises methods of treatment and compositions comprising low dose naltrexone or related opioid antagonist and mirtazepine.

In other embodiments agents may include mACh receptor antagonists, such as, for example, aripiprazole and quetiapine.

In other embodiments further agents may include serotonin reuptake inhibitors (SRIs), such as, for example, aripiprazole and vilazodone.

In other embodiments further agents may include norepinephrine reuptake inhibitors (NRIs), such as, for example, quetiapine.

In still other embodiments further agents may include selective serotonin reuptake enhancers (SSREs), such as, for example, tianeptine.

In other embodiments further agents may include sigma receptor agonists, such as, for example, opipramol.

In other embodiments further agents may include mood stabilizers, such as, for example, amisulpride, asenapine, carbamazepine, lamotrigine, lithium, olanzapine/fluoxetine, and valproic acid.

In some embodiments the present invention provides the methods and compositions that comprise triple reuptake inhibitors, e.g., dopamine, serotonin and norepinephrine.

In some embodiments, the amount of the compounds described herein or their pharmaceutically acceptable salts are admixed with the carrier materials to produce a single dosage that can vary depending upon the subject being treated and the particular mode of administration. In vitro or in vivo assays can be employed to help identify optimal dosage ranges as well as consultation with teachings that are known in the art.

The dosage of the compounds that can be used with naltrexone or related opioid antagonist (for example, as a co-administration and/or co-formulation or as a pre-existent anti-depression treatment) can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the compounds being administered, the time of administration, the route of administration, the nature of the formulation, the rate of excretion, the particular depression and/or mood disease being treated and the severity of the disorder. Some variations in the dosage can be expected.

In some embodiments, when orally administered to a mammal, the dosage of the compounds to be given with naltrexone or related opioid antagonist (for example, as a co-administration and/or co-formulation or as a pre-existent anti-depression treatment) may be 0.001 mg/kg/day to 100 mg/kg/day, 0.01 mg/kg/day to 50 mg/kg/day, or 0.1 mg/kg/day to 10 mg/kg/day. In some embodiments, when orally administered to a human, the dosage of a compound of the invention and/or additional therapeutic may be 0.001 mg to 1000 mg per day, 1 mg to 600 mg per day, or 5 mg to 30 mg per day.

In some embodiments, when administered by parenteral injection to a mammal, the dosage of the compounds to be given with naltrexone or related opioid antagonist (for example, as a co-administration and/or co-formulation or as a pre-existent anti-depression treatment) may be 0.1 mg to 250 mg per day, 1 mg to 20 mg per day, or 3 mg to 5 mg per day. Injections may be given up to four times daily.

The doses of low dose naltrexone or related agents are described herein. In general, the doses of other agents that are useful are known to those in the art (for example, those skilled in psychopharmacology). For example, doses, of for example agents described herein for combination use with low dose naltrexone, may be determined with reference *Physicians' Desk Reference,* 66th Edition, PDR Network; 2012 Edition (Dec. 27, 2011), the contents of which are incorporated by reference in its entirety. For example, a suitable dosage may be in a range of about 0.1 mg/kg to about 100 mg/kg of body weight of the subject, for example, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween In one aspect, the present invention provides a method of preventing or treating breakthrough depression in a patient in need thereof comprising administering an effective amount of low dose naltrexone or related opioid antagonist.

In another aspect, the present invention provides a method of preventing or treating treatment-refractory depression in a patient in need thereof comprising administering an effective amount of low dose naltrexone or related opioid antagonist.

In a further aspect, the present invention provides a method of preventing or treating breakthrough depression in a patient in need thereof comprising administering an effective amount of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (SSRI).

In another aspect, the present invention provides a method of preventing or treating treatment-refractory depression in a patient in need thereof comprising administering an effective amount of low dose naltrexone or related opioid antagonist in combination with an effective amount of one or more of a dopamine active anti-depressant agent, a dopamine active augmenting agent, a serotonin-norepinephrine reuptake inhibitor (SNRI), and a selective serotonin re-uptake inhibitor (S SRI).

In various embodiments, the preventing or treating breakthrough depression and/or treatment-refractory depression comprises reduction in length of a depressive episode. In various embodiments, the preventing or treating breakthrough depression and/or treatment-refractory depression comprises recovery of an anti-depressive effect of the patient's pre-existent anti-depression treatment regimen. In still other various embodiments, the preventing or treating breakthrough depression and/or treatment-refractory depression comprises a reduction in the rate of relapse after major depressive episodes. In further various embodiments, the preventing or treating breakthrough depression and/or treatment-refractory depression comprises prevention or reversal of loss of efficacy of the patient's pre-existent anti-depression treatment. In various embodiments, the preventing or treating breakthrough depression and/or treatment-refractory depression comprises reduction in an effective dosage of the patient's pre-existent anti-depression treatment, which may, for example, causes one or more of a reduction in side effects and an increase in patient adherence.

The efficacy of treating depression (e.g., breakthrough depression and/or treatment-resistant or treatment-refractory depression) using methods and compositions of the present invention may be assessed by various methods. For example, information about grading of clinical effect can be found in Cusin, Yang, Yeung, and Fava, Rating Scales for Depression (Chapter 2) in *Handbook of Clinical Rating Scales and Assessment in Psychiatry and Mental Health* (Humana, 2010), Baer and Blias, eds., the contents of which are hereby incorporated by reference in their entirety.

In some embodiments, efficacy of treatment on depression is assessed by the Hamilton Rating Scale for Depression, for example, a 17-item or 28-item Hamilton Rating Scale for Depression (HAM-D-17 or HAM-D-28). In an embodiment, efficacy may be demonstrated by a reduction in HAM-D-17 score of at least about 50%, about 55%, about 60%, about 65%, about 70%, about 75%, about 80%, about 85%, about 90%, about 95%, or about 100%, which signify improved response to treatment. Alternatively, efficacy may be demonstrated by a HAM-D-17 score of less than about 15, about 14, about 13, about 12, about 11, about 10, about 9, about 8, about 7.5, about 7, about 6.5, about 6, about 5.5, about 5, about 4.5, about 4, about 3.5, about 3, about 2.5, about 2, about 1.5, about 1, which signify increased remission following treatment. In some embodiments, the pre-treatment patient has a HAM-D-17 score of greater than about 23, or between about 19-23, or between about 14-18, or between about 8-13. In some embodiments. In some embodiments, the HAM-D-17 score effect size between patients not receiving low dose naltrexone or related opioid antagonist and patients receiving low dose naltrexone or related opioid antagonist is about 30, or about 25, or about 20, or about 15, or about 14, or about 13, or about 12, or about 11, or about 10, or about 9, or about 8, or about 7, or about 6, or about 5. In some embodiments, the HAM-D-17 score effect size between patients not receiving low dose naltrexone or related opioid antagonist and patients receiving low dose naltrexone or related opioid antagonist is between about 5 to about 15 or about 5 to about 10. In some embodiments, the low dose naltrexone or related opioid antagonist causes any of the above reductions in HAM-D-17 score within about 7 days, or about 10 days, or about 14 days from initiation of treatment with low dose naltrexone or related opioid antagonist. In some embodiments, any of the above reductions in HAM-D-17 score mediated by the low dose naltrexone or related opioid antagonist is durably maintained in the patient (e.g. for about, or greater than about, 3 weeks, or about, or greater than about, 1 month, or about, or greater than about, 2 months, or about, or greater than about, 3 months, or about, or greater than about, 6 months, or about, or greater than about, 1 year). In an embodiment, efficacy may be demonstrated by a reduction in HAM-D-28 score of at least about 50%, about 55%, about 60%, about 65%, about 70%, about 75%, about 80%, about 85%, about 90%, about 95%, or about 100%, which signify improved response to treatment. Alternatively, efficacy may be demonstrated by a HAM-D-28 score of less than about 15, about 14, about 13, about 12, about 11, about 10, about 9, about 8, about 7.5, about 7, about 6.5, about 6, about 5.5, about 5, about 4.5, about 4, about 3.5, about 3, about 2.5, about 2, about 1.5, about 1, which signify increased remission following treatment. In some embodiments, the pre-treatment patient has a HAM-D-28 score of greater than about 23, or between about 19-23, or between about 14-18, or between about 8-13. In some embodiments. In some embodiments, the HAM-D-28 score effect size between patients not receiving low dose naltrexone or related opioid antagonist and patients receiving low dose naltrexone or related opioid antagonist is about 30, or about 25, or about 20, or about 15, or about 14, or about 13, or about 12, or about 11, or about 10, or about 9, or about 8, or about 7, or about 6, or about 5. In some embodiments, the HAM-D-28 score effect size between patients not receiving low dose naltrexone or related opioid antagonist and patients receiving low dose naltrexone or related opioid antagonist is between about 5 to about 15 or about 5 to about 10. In some embodiments, the low dose naltrexone or related opioid antagonist causes any of the above reductions in HAM-D-28 score within about 7 days, or about 10 days, or about 14 days from initiation of treatment with low dose naltrexone or related opioid antagonist. In some embodiments, any of the above reductions in HAM-D-28 score mediated by the low dose naltrexone or related opioid antagonist is durably maintained in the patient (e.g. for about, or greater than about, 3 weeks, or about, or greater than about, 1 month, or about, or greater than about, 2 months, or about, or greater than about, 3 months, or about, or greater than about, 6 months, or about, or greater than about, 1 year).

In some embodiments, efficacy of treatment on depression is assessed by the Montgomery-Asberg Depression Rating Scale, for example, a 10-item or 15-item Hamilton Rating Scale for Depression (MADRS-10 or MADRS-15). In an embodiment, efficacy may be demonstrated by a reduction in MADRS-10 score of at least about 50%, about 55%, about 60%, about 65%, about 70%, about 75%, about 80%, about 85%, about 90%, about 95%, or about 100%, which signify improved response to treatment. Alternatively, efficacy may be demonstrated by a MADRS-10 score of less than about 15, about 14, about 13, about 12, about 11, about 10, about 9, about 8, about 7.5, about 7, about 6.5, about 6, about 5.5, about 5, about 4.5, about 4, about 3.5, about 3, about 2.5, about 2, about 1.5, about 1, which signify increased remission following treatment. In some embodiments, the pre-treatment patient has a MADRS-10 score of greater than about 34, or between about 20-34, or between about 7-19. In some embodiments. In some embodiments, the MADRS-10 score effect size between patients not receiving low dose naltrexone or related opioid antagonist and patients receiving low dose naltrexone or related opioid antagonist is about 40, or about 35, or about 30, or about 25, or about 20, or about 15, or about 14, or about 13, or about 12, or about 11, or about 10, or about 9, or about 8, or about 7, or about 6, or about 5. In some embodiments, the MADRS-10 score effect size between patients not receiving low dose naltrexone or related opioid antagonist and patients receiving low dose naltrexone or related opioid antagonist is between about 5 to about 15 or about 5 to about 10. In some embodiments, the low dose naltrexone or related opioid antagonist causes any of the above reductions in MADRS-10 score within about 7 days, or about 10 days, or about 14 days from initiation of treatment with low dose naltrexone or related opioid antagonist. In some embodiments, any of the above reductions in MADRS-10 score mediated by the low dose naltrexone or related opioid antagonist is durably maintained in the patient (e.g. for about, or greater than about, 3 weeks, or about, or greater than about, 1 month, or about, or greater than about, 2 months, or about, or greater than about, 3 months, or about, or greater than about, 6 months, or about, or greater than about, 1 year).

In an embodiment, efficacy may be demonstrated by a reduction in MADRS-15 score of at least about 50%, about 55%, about 60%, about 65%, about 70%, about 75%, about 80%, about 85%, about 90%, about 95%, or about 100%, which signify improved response to treatment. Alternatively, efficacy may be demonstrated by a MADRS-15 score of less than about 15, about 14, about 13, about 12, about 11, about 10, about 9, about 8, about 7.5, about 7, about 6.5, about 6, about 5.5, about 5, about 4.5, about 4, about 3.5, about 3, about 2.5, about 2, about 1.5, about 1, which signify increased remission following treatment. In some embodiments, the pre-treatment patient has a MADRS-15 score of greater than about 34, or between about 20-34, or between about 7-19. In some embodiments. In some embodiments, the MADRS-15 score effect size between patients not receiving low dose naltrexone or related opioid antagonist and patients receiving low dose naltrexone or related opioid antagonist is about 40, or about 35, or about 30, or about 25, or about 20, or about 15, or about 14, or about 13, or about 12, or about 11, or about 10, or about 9, or about 8, or about 7, or about 6, or about 5. In some embodiments, the MADRS-15 score effect size between patients not receiving low dose naltrexone or related opioid antagonist and patients receiving low dose naltrexone or related opioid antagonist is between about 5 to about 15 or about 5 to about 10. In some embodiments, the low dose naltrexone or related opioid antagonist causes any of the above reductions in MADRS-15 score within about 7 days, or about 10 days, or about 14 days from initiation of treatment with low dose naltrexone or related opioid antagonist. In some embodiments, any of the above reductions in MADRS-15 score mediated by the low dose naltrexone or related opioid antagonist is durably maintained in the patient (e.g. for about, or greater than about, 3 weeks, or about, or greater than about, 1 month, or about, or greater than about, 2 months, or about, or greater than about, 3 months, or about, or greater than about, 6 months, or about, or greater than about, 1 year).

In some embodiments, efficacy of treatment on depression is assessed by the Clinical Global Impressions—Severity and Improvement (CGI-S and CGI-I) score. In an embodiment, efficacy may be demonstrated by a reduction in CGI-S score to about 4, about 3.5, about 3, about 2.5, about 2, about 1.5, about 1, or about 0.5, which signify clinical response. In an embodiment, efficacy may be demonstrated by a reduction in CGI-I score to about 4, about 3.5, about 3, about 2.5, about 2, about 1.5, about 1, or about 0.5, which signify clinical response and improvement. In some embodiments, the pretreatment patient has a CGI-S or CGI-I score effect size between patients not receiving low dose naltrexone or related opioid antagonist and patients receiving low dose naltrexone or related opioid antagonist is about 1.5, or about 1.3, or about 1.0, or about 0.7, or about 0.5. In some embodiments, the low dose naltrexone or related opioid antagonist causes any of the above reductions in CGI-S or CGI-I score within about 7 days, or about 10 days, or about 14 days from initiation of treatment with low dose naltrexone or related opioid antagonist. In some embodiments, any of the above reductions in CGI-S or CGI-I score mediated by the low dose naltrexone or related opioid antagonist is durably maintained in the patient (e.g. for about, or greater than about, 3 weeks, or about, or greater than about, 1 month, or about, or greater than about, 2 months, or about, or greater than about, 3 months, or about, or greater than about, 6 months, or about, or greater than about, 1 year).

In various aspects, the present invention relates to compositions, pharmaceutical compositions, and formulations comprising naltrexone or related opioid antagonist. In various embodiments, the present invention provides pharmaceutical compositions, and formulations comprising naltrexone or related opioid antagonist and one or more additional agent. In some embodiments, the additional agent is a compound described herein. By way of non-limiting example, the additional agent may be a dopamine active anti-depressant agent, a dopamine active augmenting agent, a serotonin-norepinephrine reuptake inhibitor (SNRT), and a selective serotonin re-uptake inhibitor (SSRI).

The compounds described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term pharmaceutically acceptable salt also refers to a salt of the compounds of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

The compositions described herein or their pharmaceutically acceptable salts which are used in accordance with the present invention may exhibit stereoisomerism by virtue of the presence of one or more asymmetric or chiral centers in the compounds. The present invention contemplates the various stereoisomers and mixtures thereof. Desired enantiomers can be obtained by chiral synthesis from commercially available chiral starting materials by methods well known in the art, or may be obtained from mixtures of the enantiomers by resolution using known techniques.

The compounds described herein or their pharmaceutically acceptable salts can be administered to a subject in need thereof as a component of a composition that comprises a pharmaceutically acceptable carrier or vehicle.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the compounds of present invention or their pharmaceutically acceptable salts are administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, sodium chloride, dried skim milk, glycerol, propylene, glycol, water, ethanol and the like. The present compositions, if desired, can also comprise minor amounts of wetting or emulsifying agents, or pH buffering agents.

The present compositions and/or additional therapeutics agents can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference in its entirety.

In one embodiment, the compounds described herein are formulated in accordance with routine procedures as a composition adapted for oral administration to human beings. Compositions for oral delivery can be in the form of tablets (by way of non-limiting example, REVIA), lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active compound of the invention are also suitable for oral administration. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the compounds described herein or their pharmaceutically acceptable salts can be formulated for intravenous administration. Typically, compositions for intravenous administration comprise a sterile isotonic aqueous buffer. Where necessary, the compositions can also include a solubilizing agent. Compositions for intravenous administration can optionally include a local anesthetic such as lignocaine to lessen pain at the site of the injection.

Generally, the ingredients are supplied either separately or mixed together in unit dosage form, for example, as a dry lyophilized-powder or water-free concentrate in a hermetically sealed container such as an ampule or sachette indicating the quantity of active agent. Where the compounds described herein or their pharmaceutically acceptable salts are to be administered by infusion, they can be dispensed, for example, with an infusion bottle containing sterile pharmaceutical grade water or saline. Where the compounds described herein or their pharmaceutically acceptable salts are administered by injection, an ampule of sterile water for injection or saline can be provided so that the ingredients can be mixed prior to administration.

Where the compounds described herein or their pharmaceutically acceptable salts can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the compounds mentioned herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, concentration or availability of enzymes, concentration or availability of water, or other physiological conditions or compounds.

Compositions can be prepared according to conventional mixing, granulating or coating methods, respectively, and the present compositions can comprise, in one embodiment, from about 0.1% to about 99%; and in another embodiment from about 1% to about 70% of the compounds described herein or their pharmaceutically acceptable salts by weight or volume.

In some embodiments, low dose naltexone or other compounds described herein may be administered to a subject for a period of about 1, about 2, about 3, about 4, about 5, about 6, about 7, about 8, about 9, about 10, about 11, or about 12 months, or about 2, about 3, about 4, about 5, about 6, about 7, about 8, about 9, about 10 years. In some embodiments, low dose naltexone or other compounds described herein may be administered to a subject chronically.

In another embodiment, the compounds described herein or their pharmaceutically acceptable salts act synergistically when co-administered with another therapeutic agent and are administered at doses that are lower than the doses commonly employed when such agents are used as monotherapy. The dosage of compounds described herein or their pharmaceutically acceptable salts as well as the dosing schedule can depend on various parameters, including, but not limited to, the depression and/or mood disorder being treated, the subject's general health, and the administering physician's discretion. The compounds described herein or their pharmaceutically acceptable salts, such as, for example, naltrexone or related opioid antagonist, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic, such as, for example, one or more of a dopamine active anti-depressant agent, a dopamine active augmenting agent, a serotonin-norepinephrine reuptake inhibitor (SNRI), and a selective serotonin re-uptake inhibitor (SSRI), to a subject in need thereof. In various embodiments, the compounds described herein or their pharmaceutically acceptable salts are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

Methods of administration include but are not limited to oral, subcutaneous, intradermal, intramuscular (by way of non-limiting example, intramuscular depot, such as, for instance, as described in U.S. Pat. No. 6,569,449, the contents of which are hereby incorporated by reference in its entirety), intraperitoneal, intravenous, intranasal, epidural, sublingual, intranasal, intracerebral, intravaginal, transdermal, rectally, by inhalation, or topically, particularly to the ears, nose, eyes, or skin. The mode of administration can be left to the discretion of the practitioner. In most instances, administration results in the release of the compounds described herein or their pharmaceutically acceptable salts into the bloodstream.

The compounds described herein or their pharmaceutically acceptable salts can be administered orally. The compounds described herein or their pharmaceutically acceptable salts can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the compounds described herein or their pharmaceutically acceptable salts.

In yet another embodiment, the compounds described herein or their pharmaceutically acceptable salts can be delivered in a controlled release system. In one embodiment, a pump may be used (see Langer, 1990, *Science* 249:1527-1533; Sefton, 1987, CRC Crit. *Ref Biomed. Eng.* 14:201; Buchwald et al., 1980, *Surgery* 88:507; Saudek et al., 1989, *N. Engl. J. Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). Other controlled-release systems discussed in the review by Langer, 1990, *Science* 249:1527-1533) may be used.

Administration of the described compounds or their pharmaceutically acceptable salts can, independently, be one to four times daily or one to four times per month or one to six times per year or once every two, three, four or five years. Administration can be for the duration of one day or one month, two months, three months, six months, one year, two years, three years, and may even be for the life of the subject. Chronic, long-term administration will be indicated in many cases. The dosage may be administered as a single dose or divided into multiple doses.

The dosage regimen utilizing the described compounds or their pharmaceutically acceptable salts can be selected in accordance with a variety of factors including type, species, age, weight, sex and medical condition of the subject; the severity of the condition to be treated; the route of administration; the renal or hepatic function of the subject; and the specific compound of the invention employed. The described compounds or their pharmaceutically acceptable salts can be administered in a single daily dose, or the total daily dosage can be administered in divided doses of two, three or four times daily. The compounds described herein or their pharmaceutically acceptable salts and/or additional therapeutic can be assayed in vitro or in vivo for the desired therapeutic or prophylactic activity prior to use in humans. Animal model systems can be used to demonstrate safety and efficacy.

The term subject, as used herein unless otherwise defined, is a mammal, e.g., a human, mouse, rat, guinea pig, dog, cat, horse, cow, pig, or non-human primate, such as a monkey, chimpanzee, or baboon. The terms "subject" and "patient" are used interchangeably. In some embodiments, a subject is a human suffering from a type of depression described herein who does not also suffer from alcohol or drug dependence.

In one embodiment, the subject is a human. In some embodiments, the human is a pediatric human. In other embodiments, the subject is an adult human.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In addition to treating pre-existing depression and/or mood disorders and/or other disorders descried herein, the described compounds or their pharmaceutically acceptable salts can be administered prophylactically in order to prevent or slow the onset of these disorders. In prophylactic applications, the described compounds or their pharmaceutically acceptable salts can be administered to a subject susceptible to or otherwise at risk of a particular depression and/or mood disorder and/or other disorders descried herein.

In another embodiment, an outcome of the methods of the present invention is rapid antidepressant response as compared to the usual latency for response to traditional antidepressant pharmacotherapy. Such a response can be less than about 1 day, or about 2 days, or about 3 days, or about 4 days, or about 5 days, or about 6 days, or about 7 days, or about 10 days, or about 2 weeks. In some embodiments, the latency for response to traditional antidepressant pharmacotherapy is about 3, or about 4, or about 5, or about, 6 weeks, or about 8, or about 10 weeks.

The invention also provides kits that can simplify the administration of the described compounds or their pharmaceutically acceptable salts, to a subject.

A typical kit of the invention comprises the described compounds or their pharmaceutically acceptable salts, for example, in unit dosage form. In one embodiment, the unit dosage form is a container, which can be sterile, containing an effective amount of a described compound or their pharmaceutically acceptable salts and a pharmaceutically acceptable carrier, diluent, excipient, or vehicle. The kit can further comprise a label or printed instructions instructing the use of described compounds or their pharmaceutically acceptable salts to treat or prevent depression and/or mood disorders and/or other disorders descried herein. The kit can also further comprise one or more additional therapeutic agents, for example, in unit dosage form, such as a container containing an effective amount of the other therapeutic agent. In one embodiment, the kit comprises a container containing an effective amount of naltrexone or related opioid antagonist or a pharmaceutically acceptable salt thereof and an effective amount of another therapeutic agent. Examples of other therapeutic agents include, but are not limited to, those listed herein.

This invention is further illustrated by the following non-limiting examples.

EXAMPLES

Example 1

Patient Responses to Low Dose Naltrexone Treatment of Depression

Patient #1: A middle aged female suffered severe depression with recurrent major depressive episodes. She had responded briefly to complex polypharmacy and electroconvulsive therapy, but depression usually returned within 3 weeks of these interventions. In addition to restarting aripiprazole (ABILIFY), to which she had transiently responded in the past, the patient was instructed to pulverize a tablet of naltrexone 50 mg, and take the smallest fragment with water. A sample of these fragments was later weighed, indicating she was taking on the average about 1 mg of naltrexone daily. The former pharmacologic regimen was otherwise unchanged.

About one week after initiating low dose naltrexone, the patient experienced marked remission. Despite minor variation in mood, she has maintained the remission for more than 6 months (continuing to present). She has remained on adjunctive naltrexone 1 mg daily.

Patient #2: A particularly treatment-resistant patient with a depressive recurrence, was administered approximately 1 mg daily of naltrexone to a complex antidepressant regimen, which included duloxetine and riluzole. This patient demonstrated a robust response within 2 weeks, which has now been maintained for over 2 years.

Patient #3: A female patient in her 50s presented with treatment-resistant depression. The patient was also diagnosed with Attention Deficit Disorder. The patient initially was treated with s-citalopram 15 mg, augmented by dextroamphetamine. She responded briefly but rapidly returned to depressed mood with attention deficits. When naltrexone 1 mg was added to her treatment regime, the patient experienced a marked lifting of mood, noting that her attention was also much improved. This response was seen within days of the addition of naltrexone. She reported no adverse effects.

Patient #4: A 62-year-old female patient weighing approximately 60 kg had suffered severe unremitting depression. She was treated with and responded to electro-convulsive therapy, but regressed within a week. Complex pharmacotherapy, including s-citalopram augmented by aripiprazole and mirtazepine, led to only transient response, with depressive symptoms returning after several days. Subsequently, the patient was prescribed 5 mg naltrexone daily with continuation of s-citalopram. The patient has remained euthymic during more than two months of observation.

Patient #5: A female patient in her 40s had suffered severe treatment-resistant depression, exhibiting low energy, crying, unable to obtain and maintain employment, and anhedonia. She was being treated with buproprion XL 300 mg, augmented with melatonin 3 mg and N-acetyl-cysteine 1200 mg. The patient was then co-administered naltrexone 1 mg, and within two weeks, she experienced marked remission. After five months and continuing, she is no longer crying has improved motivation and interests, and has obtained meaningful employment.

Patient #6: A male patient in his 80s with multiple major depression episodes, anhedonia, apathy, low energy and poor sleep was being treated with duloxetine 60 mg and buproprion 75 mg, and mirtazpine 15 mg. Naltrexone 1 mg was added, and within one week, the patient felt much better, stating that adding the naltrexone has a unique effect. The patient also reported that he had more energy, was sleeping better, was sexually active, and had returning interest in his hobby.

Patient #7: A female patient in her late 50s with a brain tumor, epilepsy and somatization disorder, also demonstrated multiple depression episodes. She rarely left her couch, lived in social isolation, often cried, did not shower or get dressed. She also called and e-mailed multiple times per day. She was being treated with Effexor XR 75 mg QHS, Xanax 0.5 mg, and Clonazepam 1.5 mg. After adding naltrexone 1 mg, and gabapentin 300 mg and melatonin 5 mg, within three weeks, the patient was able to obtain employment, was socializing with friends, was less anxious. Her crying episodes were replaced with smiling and laughing.

Patient #8: A treatment-resistant patient with depressive recurrence was being treated with pramipexole with limited benefit. The patient was then co-administered 1 mg daily of naltrexone with pramipexole. The patient demonstrated a robust response within a few weeks.

Patient #9: A middle-age female suffered severe depression with recurrent major depressive episodes and social anxiety. She was being treated with Adderall 10 mg, levothyroxine 50 mcg, and propranol 10 mg. Naltrexone 1 mg was added to her regimen, and she experienced improvement in her depression.

Example 2

Clinical Testing of Low Dose Naltrexone Treatment of Depression

The clinical studies described herein, in part, assess the magnitude and rate of response to low dose naltrexone, as measured by change on the Hamilton Rating Scale for Depression (HAM-D-17 or HAM-D-28), compared to placebo. Additional assessments are based on the Montgomery-Asberg Depression Rating Scale (MADRS-10 or MADRS-15) and Clinical Global Impressions—Severity and Improvement (CGI-S and CGI-I).

The trial was conducted over 6 weeks, with double-blind treatment based on random assignment to low dose naltrexone or placebo. To assess longevity of response to Low Dose Naltrexone, patients assigned to active drug were followed for 6 weeks, but the design did not provide a contrasting placebo group beyond 3 weeks.

12 men and women ages 25 to 64 who received antidepressant regimens including at least one dopaminergic agent (an NDRI, pramipexole, aripiperazole at less than or equal to 2 mg, amphetamine salt, methylphenidate, or sertraline at 150 mg or greater), had achieved remission for at least 3 months followed by relapse or recurrence, were recruited. All ethnicities were included.

Inclusion criteria included an age of 18-65; written informed consent; patients meet DSM-IV criteria (by Structured Clinical Interview for DSM-IV SCID-UP) for MDD, current; Quick Inventory of Depressive Symptomatology—Self-Rated (QIDS-SR) score of at least 12 at both screen and baseline visits; received treatment with SSRI in combination with a dopaminergic agent; or on an antidepressant with a dopaminergic mechanism of action, including SNRIs, MAOIs, TCAs, or bupropion, in adequate doses, achieved remission per ACNP Task Force guidelines (REF) for ≥3 months, currently in relapse or recurrence without dose change for at least the past 4 weeks, based on meeting DSM-IV criteria for MDD.

Dopaminergic agents here included, for example, classical stimulants from the amphetamine or methylphenidate families; the wakefulness promoting agents, modafinil and armodafinil; dopamine agonists (e.g. pramipexole); or bupropion (≥300 mg/day to ensure significant dopamine reuptake inhibition). Additionally, low dose (≤2.5 mg) Abilify, a $D_2$ partial agonist, was included as a dopamine agent. Sertraline, classified as an SSRI, had dopamine reuptake inhibiting properties believed to be relevant at higher doses (≥150 mg) and was therefore considered a dopaminergic agent, as well as allowed as SSRI monotherapy at dopaminergic doses. SNRIs (e.g. venlafaxine) and TCAs (e.g. nortriptyline) were known to have prominent inhibitory effects on the reuptake of norepinephrine; however, since the norepinephrine transporter was responsible for both norepinephrine and dopamine reuptake in the prefrontal cortex, these agents were also considered to be pro-dopaminergic antidepressants.

During the baseline visit, patients were on a stable dose of antidepressant regimen for the past 4 weeks.

Once patients agreed to participate in the study by signing the informed consent document, a full medical and psychiatric history was taken and a physical examination was performed by a board-certified psychiatrist. Screen rating scales were performed. Screened and eligible patients were asked to return one week later for a baseline visit when they are randomized to double-blind treatment with placebo or low dose naltrexone, with the study design outlined above. The study lasted six weeks, during which patients were assessed weekly. Subjects were assigned randomization numbers in consecutive order. The randomization list was provided by a computer-generated random-number list and was maintained by the research pharmacist. In addition, the presence of any side effect or adverse event was carefully documented with the SAFTEE-SI. Reasons for premature discontinuation, including change in primary medications, were recorded.

All concomitant medications taken during the study were recorded in the case report form, along with dosage information and start and stop dates. Medication management and clinical ratings were performed by the study clinicians.

At the end of the double-blind study, both responders and non-responders who completed the double-blind phase had the option of receiving open-label adjunctive treatment with low dose naltrexone. Subjects who agreed to receive open-label treatment with low dose naltrexone for 3 months were seen monthly by a board-certified psychiatrist until the end of the follow-up phase. Subjects who completed or refused follow-up were offered a referral to a psychiatrist.

The primary efficacy measurement was the change in 17-item Hamilton Rating Scale for Depression (HAM-D-17) score or the 28-item Hamilton Rating Scale for Depression (HAM-D-28). Secondary measures of efficacy include change in CGI-severity, with clinical or CGI-improvement (CGI-I). An additional measure of efficacy was the change in Montgomery-Asberg Depression Rating Scale (MADRS-10 or MADRS-15).

The following instruments were administered according to the study schedule: a structured clinical interview for DSM-IV, an antidepressant treatment history questionnaire, the 17-item or 28-item Hamilton Depression Scale (HAM-D-17 or HAM-D-28), Clinical Global Impressions—severity and improvement (CGI-S, CGI-I), 10-item or 15-item Montgomery-Asberg Depression Rating Scale (MADRS-10 or MADRS-15), Quick inventory Depressive Symptomatology (Self Report) (QIDS-SR), a cognitive and physical functioning questionnaire, a sexual functioning questionnaire, the Quality of Life Satisfaction Questionnaire-short form (Q-LES-Q), and the Sheehan Disability Scale.

Figure 1B:
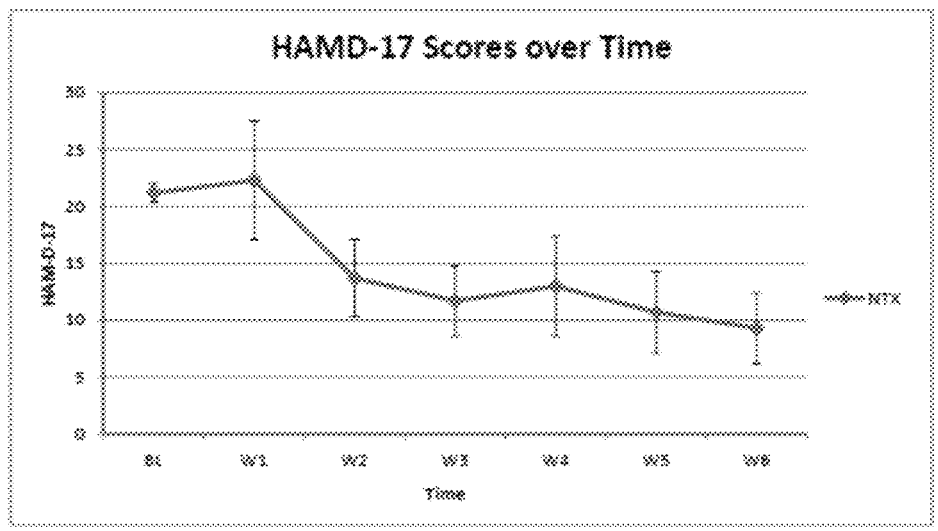
Figure 2A:
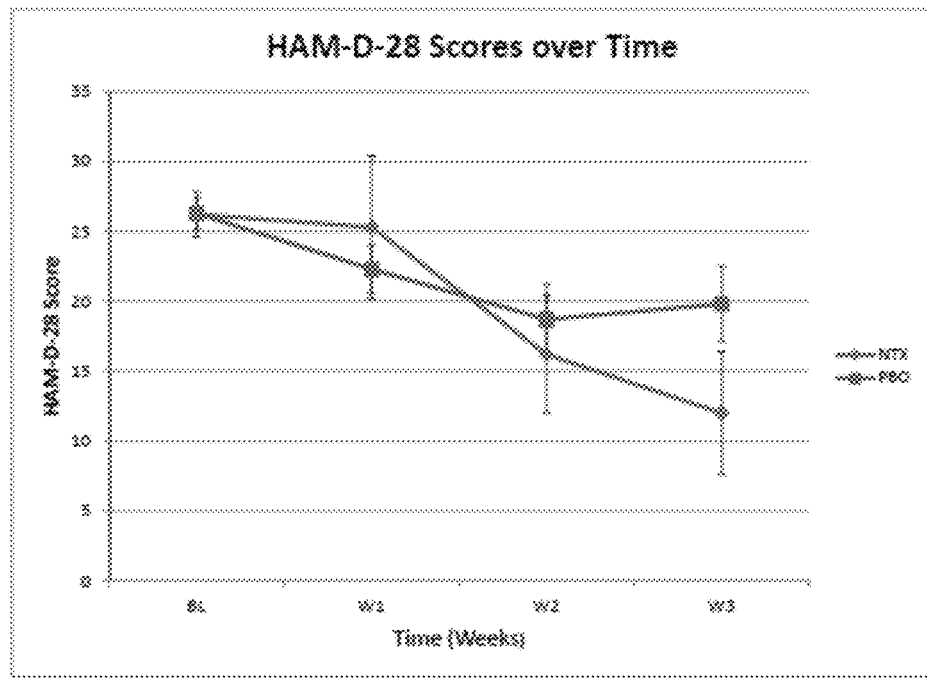
FIGS. 2A and 2B show patient response during clinical testing of low dose naltrexone treatment for depression as measured by 28-item Hamilton Rating Scale for Depression (HAM-D-28) over three weeks (FIG. 2A) and six weeks (FIG. 2B), respectively.
Figure 2B:
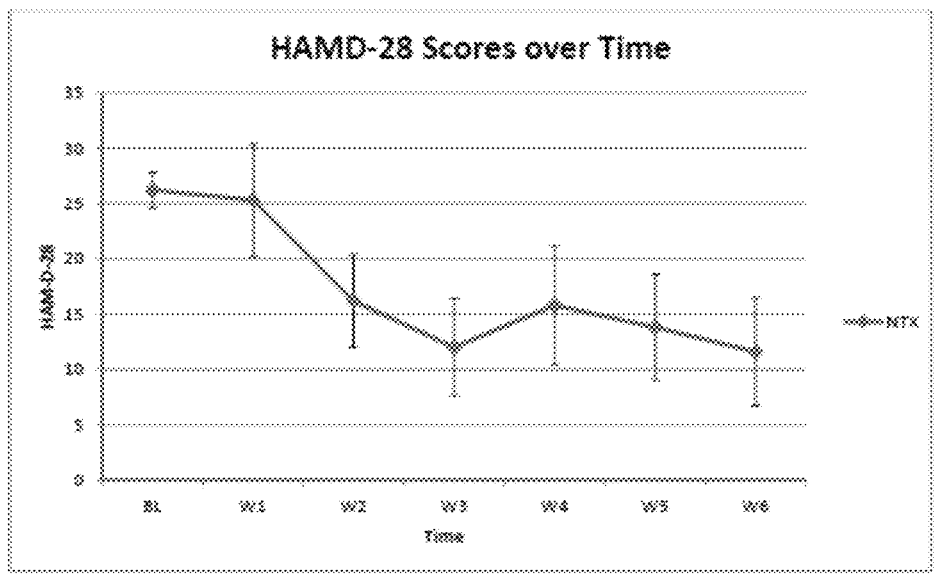
Figure 3A:
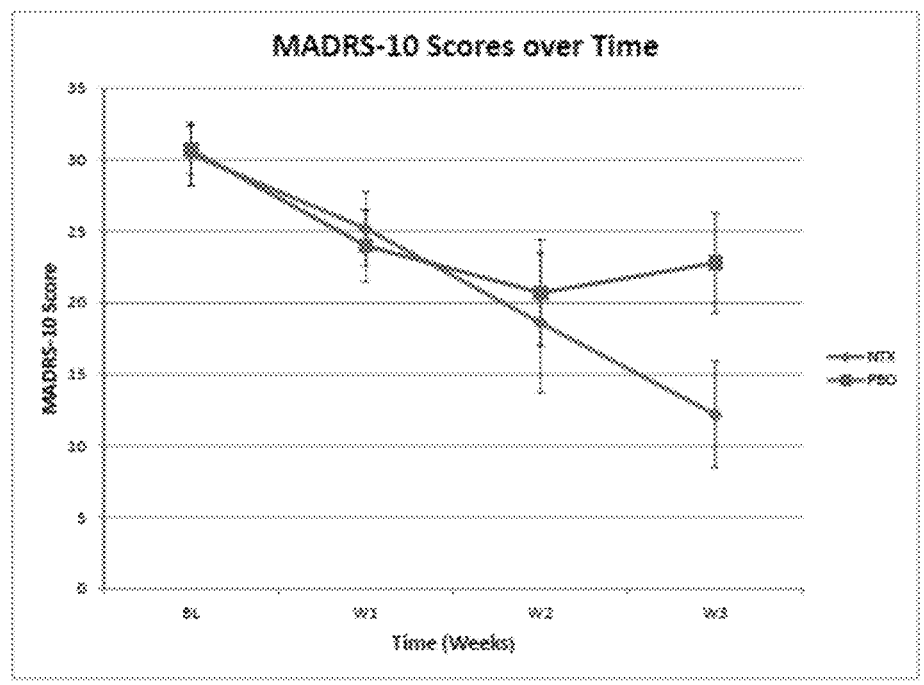
FIGS. 3A and 3B show patient response during clinical testing of low dose naltrexone treatment for depression as measured by 10-item Montgomery-Asberg Depression Rating Scale (MADRS-10) over three weeks (FIG. 3A) and six weeks (FIG. 3B), respectively.
Figure 3B:
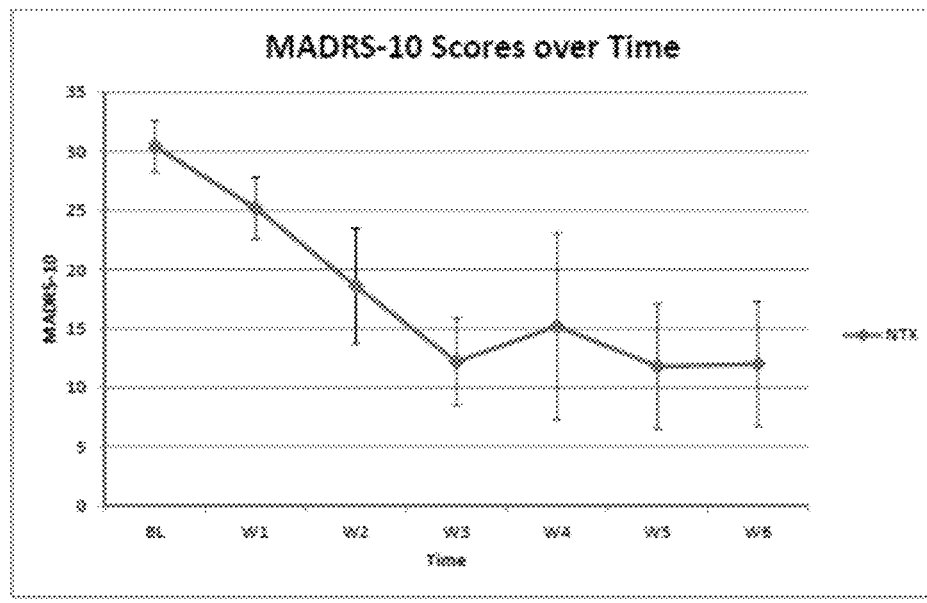
Figure 4A:
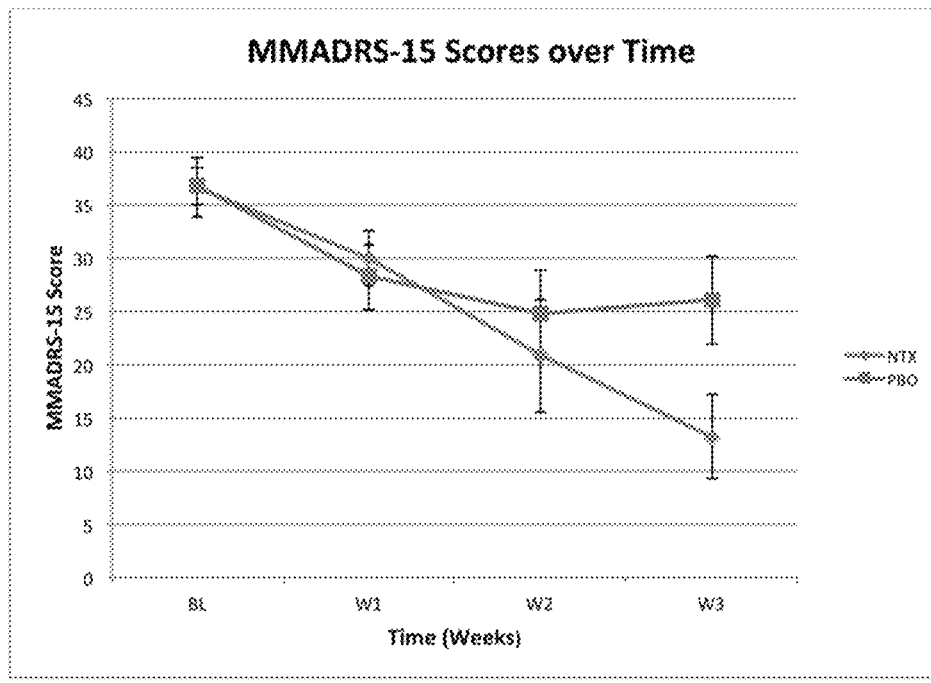
FIGS. 4A and 4B show patient response during clinical testing of low dose naltrexone treatment for depression as measured by 15-item Montgomery-Asberg Depression Rating Scale (MADRS-15) over three weeks (FIG. 4A) and six weeks (FIG. 4B), respectively.
Figure 4B:
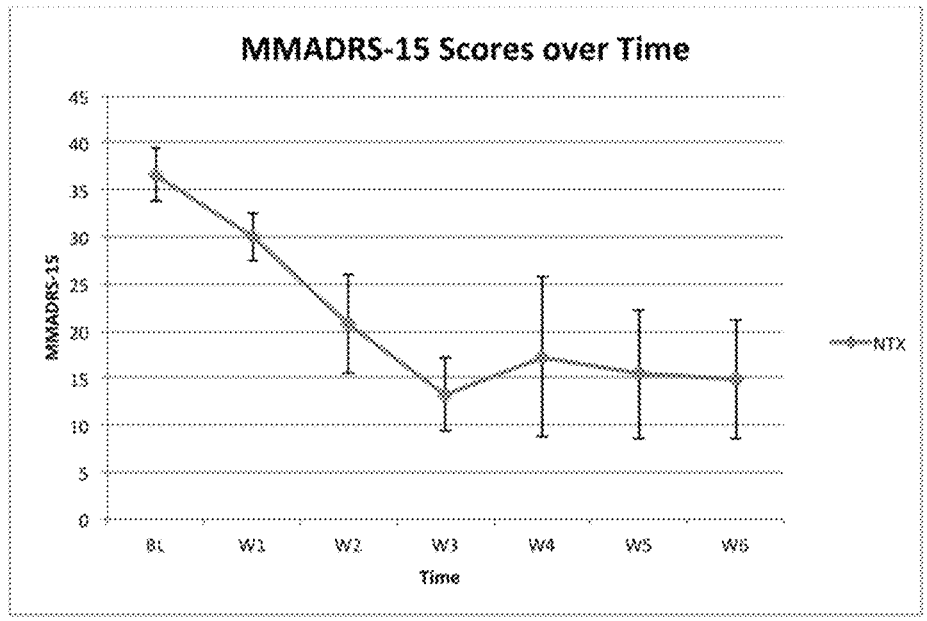
Figure 5A:
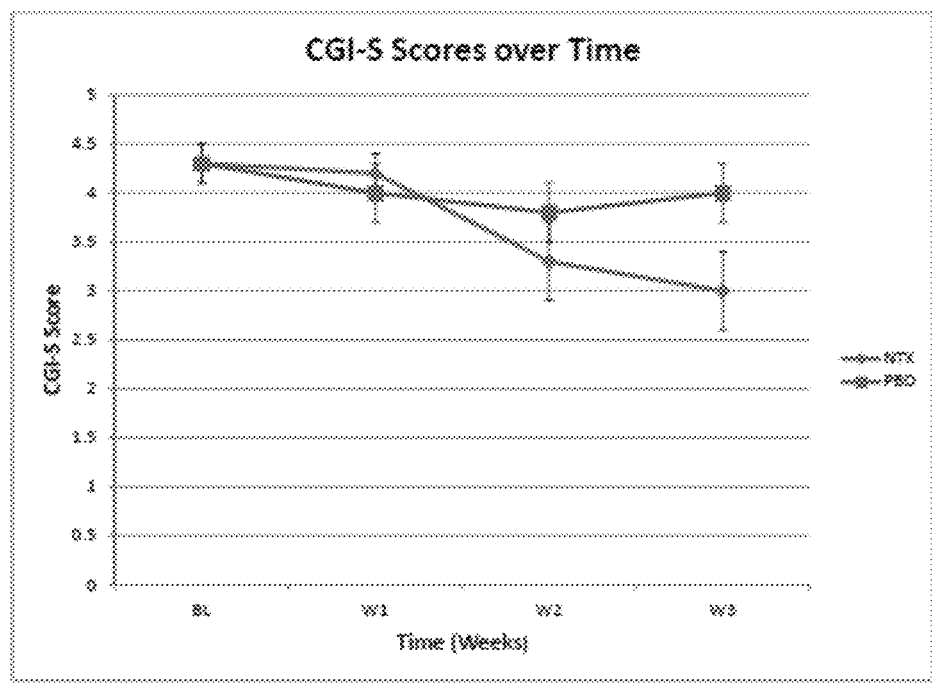
FIGS. 5A and 5B show patient response during clinical testing of low dose naltrexone treatment for depression as measured by Clinical Global Impressions—Severity (CGI-S) over three weeks (FIG. 5A) and six weeks (FIG. 5B), respectively.
Figure 5B:
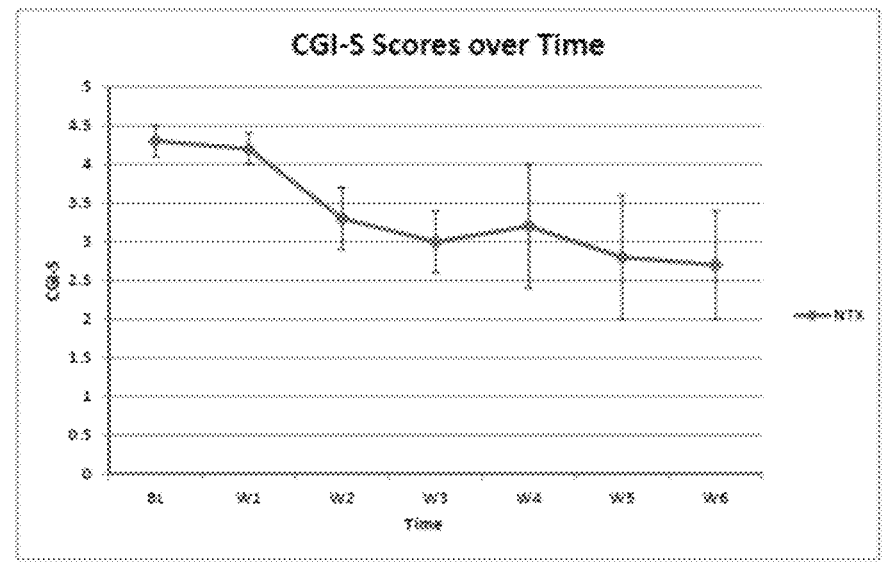
Figure 6A:
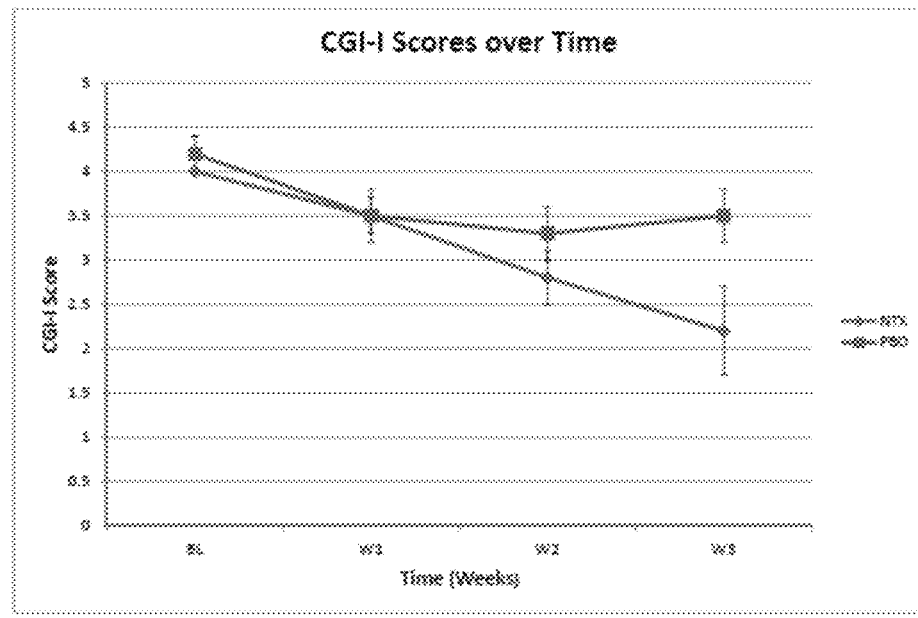
FIGS. 6A and 6B show patient response during clinical testing of low dose naltrexone treatment for depression as measured by Clinical Global Impressions—Severity Improvement (CGI-I) over three weeks (FIG. 6A) and six weeks (FIG. 6B), respectively.
Figure 6B:
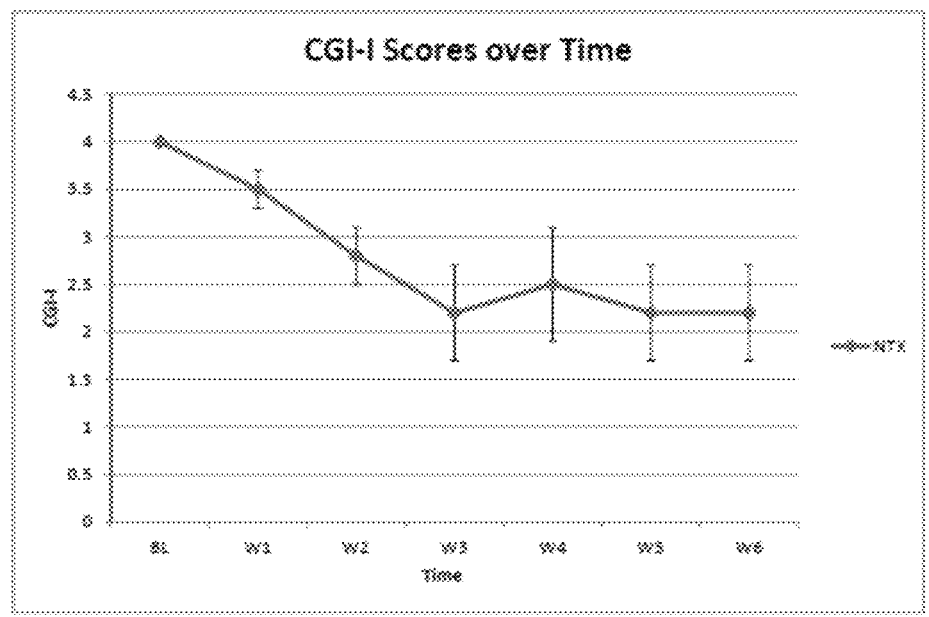

Low dose naltrexone showed specific efficacy for the treatment of "breakthrough depression," an umbrella term, which encompasses depressive relapse (a depressive episode within 6 months of antidepressant response) and recurrence (a depressive episode after 6 months of response). Patients with breakthrough depression (BTD) on an antidepressant regimen containing a pro-dopaminergic agent assigned to treatment with low dose naltrexone (1 mg bid) demonstrated higher rates of response on all outcome measures. See figures for statistical analysis (e.g. FIGS. 1A, 2A, 3A, 4A, 5A, and 6A). The response to active drug continued during the entire six week trial period (e.g. FIGS. 1B, 2B, 3B, 4B, 5B, and 6B).

Additionally, patients with BTD on an antidepressant regimen containing a pro-dopaminergic agent assigned to treatment with low dose naltrexone experienced no significant differences in the number of adverse events, as measured by the SAFTEE-SI as well as greater improvement in Quality of Life, Enjoyment, and Satisfaction Questionnaire (Q-LES-Q) and Sheehan Disability Scale (SDS) scores, compared to placebo controls.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A method for treating relapsing or recurrent major depressive disorder (MDD), comprising orally administering a therapeutically effective low dose amount of naltrexone to a human patient in need thereof, wherein:

the low dose amount of naltrexone is about 1 mg, administered once or twice daily for at least three weeks; and
the patient is undergoing treatment for MDD comprising at least one dopaminergic agent.

2. The method of claim 1, wherein the MDD is breakthrough depression.

3. The method of claim 1, wherein the dopaminergic agent is bupropion.

4. The method of claim 1, wherein the dopaminergic agent is pramipexole.

5. The method of claim 1, wherein the dopaminergic agent is aripiperazole.

6. The method of claim 1, wherein the dopaminergic agent is an amphetamine salt.

7. The method of claim 1, wherein the dopaminergic agent is methylphenidate.

8. The method of claim 1, wherein the dopaminergic agent is sertraline at a dose of above 150 mg daily.

9. The method of claim 2, wherein the treating breakthrough depression comprises a reduction in the rate of relapse after major depressive episodes.

10. The method of claim 1, wherein the treating results in a Hamilton Rating Scale for Depression (HAM-D-17) score of less than 15.

11. The method of claim 1, wherein the treating results in a Montgomery-Asberg Depression Rating Scale (MADRS-10) score of less than 15.

12. The method of claim 1, wherein the treating results in a Clinical Global Impressions Improvement (CGI-I) score of less than 3.

13. A method for treating breakthrough major depressive disorder (MDD), comprising orally administering a therapeutically effective low dose amount of naltrexone to a human patient having a remission for at least 3 months followed by a relapse or recurrence, wherein:
   the low dose amount of naltrexone is about 1 mg, administered once or twice daily for at least three weeks;
   the patient is undergoing treatment for MDD comprising at least one of bupropion, pramipexole, and aripiperazole; and
   the treating causes a reduction in the patient's Hamilton Rating Scale for Depression (HAM-D-17) to less than 15 within three weeks or less from beginning of administration of the low dose amount of naltrexone.

14. The method of claim 13, wherein the antidepressant response is observed within three weeks from beginning of administration of the low dose amount of naltrexone.

* * * * *